(12) United States Patent
Ito (10) Patent No.: US 8,013,042 B2
(45) Date of Patent: *Sep. 6, 2011

(54) PROCESS OF PRODUCING A PARTICLE HAVING A CORE-SHELL STRUCTURE

(75) Inventor: Hisayoshi Ito, Himeji (JP)

(73) Assignee: Daicel Chemical Industries, Ltd., Osaka (JP)

(*) Notice: Subject to any disclaimer, the term of this patent is extended or adjusted under 35 U.S.C. 154(b) by 394 days.

This patent is subject to a terminal disclaimer.

(21) Appl. No.: 12/365,006

(22) Filed: Feb. 3, 2009

(65) Prior Publication Data

US 2009/0149572 A1    Jun. 11, 2009

Related U.S. Application Data

(62) Division of application No. 10/580,652, filed as application No. PCT/JP2004/016655 on Nov. 10, 2004, now abandoned.

(30) Foreign Application Priority Data

Nov. 28, 2003  (JP) ................................. 2003-400821

(51) Int. Cl.
*C08L 5/00* (2006.01)
*C08L 89/00* (2006.01)
(52) U.S. Cl. ................. 524/56; 524/27; 524/47; 524/58
(58) Field of Classification Search ............ 524/27, 524/47, 56, 58
See application file for complete search history.

(56) References Cited

U.S. PATENT DOCUMENTS

| 2003/0049559 A1 | 3/2003 | Shigemori et al. |
| 2003/0065087 A1 | 4/2003 | Nambu et al. |

FOREIGN PATENT DOCUMENTS

| JP | 60-13816 A | 1/1985 |
| JP | 61-9433 A | 1/1986 |
| JP | 7-70255 A | 3/1995 |
| JP | 9-165457 A | 6/1997 |
| JP | 10-176065 A | 6/1998 |
| JP | 2001-114901 A | 4/2001 |
| JP | 2003-34725 A | 2/2003 |

*Primary Examiner* — Milton I Cano
*Assistant Examiner* — Gennadiy Mesh
(74) *Attorney, Agent, or Firm* — Birch, Stewart, Kolasch & Birch, LLP (57) ABSTRACT

A multiple particle (e.g., a spherical particle) comprising an organic solid component (A) containing a plurality of organic solid materials (e.g., polymers) is produced by eluting a water-soluble auxiliary component (B) containing at least an oligosaccharide (B1) from a composition having a disperse system, in which a particulate dispersed phase comprising the organic solid component (A) is dispersed in a matrix comprising the auxiliary component (B). The organic solid materials may be different in affinity relative to the auxiliary component (B) from each other. The particle may have a core-shell structure which comprises a core containing a first organic solid material (e.g., a hydrophobic polymer) and a shell containing a second organic solid material (e.g., a hydrophilic polymer) immiscible with the first organic solid material.

16 Claims, 2 Drawing Sheets

PROCESS OF PRODUCING A PARTICLE HAVING A CORE-SHELL STRUCTURE

CROSS REFERENCE

This application is a Divisional of U.S. application Ser. No. 10/580,652, filed on Sep. 25, 2006, now abandoned, which is the national phase of PCT/JP04/16655 filed on Nov. 10, 2004, which designated the United States and which claims priority to Japanese Application 400821/2003 filed on Nov. 28, 2003. The entire contents of the above applications are hereby incorporated by reference.

TECHNICAL FIELD

The present invention relates to a multiple particle (e.g., a multiple polymer particle) providing characteristics unachievable in a particle (e.g. a polymer particle) formed from a single component (e.g., a polymer), a dispersion composition for obtaining the multiple particle, and a process for producing the multiple particle. More specifically, the present invention also relates to a multiple particle (e.g., a microcapsule) useful for various fields such as a cosmetic, an image recording material (such as an ink or a colored particle) used for an ink jet printer or other means, a paint and varnish such as a powdered paint.

BACKGROUND ART

Heretofore, as a process for producing a polymer particle, a mechanical pulverization (or crushing) method has been utilized, which comprises, for example, crushing a polymer or polymer composition coarsely by using a crushing machine or other means, then pulverizing the crushed matter finely by using a jet mill or other means, and classifying the resultant by an air classifier or other means. In such a method, however, manufacturing machines are expensive, and additionally, thus obtained particle is irregular in shape and widely varies in particle size. In order to make the polymer particle size uniform, the obtained particle should be classified. However, unusable polymer particles in size are produced in large quantities by classification, and are unfavorable from an economical viewpoint. Further, spherical fine particles are preferred from the viewpoint of blocking among particles, dispersibility, flowability or others, however, it is impossible to obtain spherical particles by mechanical pulverization (or crushing) methods.

Moreover, Japanese Patent Application Laid-Open No. 176065/1998 (JP-10-176065A, Patent Document 1) discloses a process for obtaining a spherical fine particle of a thermoplastic resin (a), which comprises melt-kneading the thermoplastic resin (a) to be powdered with other one or more of thermoplastic resin(s) (b) to give a polymer composition comprising the resin (a) constituting the dispersed phase and the resin (b) constituting the continuous phase, and washing the polymer composition with a solvent incapable of dissolving the resin (a) and capable of dissolving the resin (b). In this process, however, it is necessary not only that the dispersed phase and the continuous phase are immiscible with each other, but also that an appropriate combination of the resin constituting the continuous phase with the solvent is selected depending on the kind of the resin of the dispersed phase. Therefore, the combination of the resins should be limited to a specific one, and in addition, the combination of the resin with the solvent should be limited to a specific one. Moreover, in the case where a fine particle comprising a plurality of resins is produced by using this process, not only the combination of resins constituting the dispersed phase and the combination of the resin constituting the dispersed phase and the resin constituting the continuous phase, but also the kind of the washing solvent or others are highly limited. In particular, in such a system, it is very difficult to obtain a multiple particle having a core-shell structure. Furthermore, the resin constituting the continuous phase is to be recovered in the end, or to be discarded in a dissolved state, as it is not included in the resin fine particle as a final product. However, recovery of the resin in the solution not only is very difficult but also is a caused factor of increase in the production cost of the polymer particle. Moreover, in the case of discarding the resin solution directly as a waste fluid, adverse effects on the environment cannot be ignored.

Japanese Patent Application Laid-Open No. 13816/1985 (JP-60-13816A, Patent Document 2) proposes a process for producing a thermoplastic polymer particle, which comprises melting a polyethylene glycol and a thermoplastic resin with stirring, putting the molten mixture into water to solidify, and then removing the polyethylene glycol from the resulting matter with water. Japanese Patent Application Laid-Open No. 9433/1986 (JP-61-9433A, Patent Document 3) discloses a process for producing a thermoplastic polymer particle, which comprises melting a thermoplastic resin and a polyethylene oxide with stirring, then cooling the molten mixture, and removing the polyethylene oxide from the mixture with water. Japanese Patent Application Laid-Open No. 165457/1997 (JP-9-165457A, Patent Document 4) discloses a process for producing a polymer fine particle, which comprises mixing a melt-formable and water-soluble polymer (such as a polyvinyl alcohol-series polymer, a denatured starch, or a polyethylene oxide) and a thermoplastic resin to give a melt-shaped product, and then removing the water-soluble polymer from the shaped product with water.

Even in these processes, however, since it is necessary that a resin and a water-soluble polymer are immiscible with each other, a selectable combination of the resins is limited, and in addition, the particle size distribution of thus resulting polymer particle is insufficient in uniformity. In particular, in the case of forming a polymer particle comprising a plurality of resins, the species of raw material to be used is highly limited because the combination of the resin and the water-soluble polymer also exerts a great influence on formation of the polymer particle. Further, these water-soluble polymers having small solubilities to water need a large amount of water for dissolution, and in addition, significantly deteriorate productivity of polymer particles due to the low velocity of dissolution. Furthermore, since such water-soluble polymers are often derived from unnatural products, a waste fluid containing such a water-soluble polymer dissolved therein adversely affects on the environment.

On the other hand, as a process for obtaining a polymer fine particle having a core-shell structure, a seeded emulsion polymerization, comprising polymerization of a polymerizable monomer after synthesizing a polymer fine particle as a core, is most popularly practiced. For example, Japanese Patent Application Laid-Open No. 70255/1995 (JP-7-70255A, Patent Document 5) discloses a production process of a core-shell polymer having an alkyl acrylate-series rubber-like core and a methyl methacrylate-series glass-like shell.

In the seeded emulsion polymerization, however, it is difficult to stably produce a particle having a particle size over 1 μm and a narrow particle size distribution, further the polymer available for the seed polymerization is limited to a polymer obtained from a radical-polymerizable monomer. Therefore, the seeded emulsion polymerization cannot be employed to a polymer obtained by a condensation reaction, or a curing or crosslinking reaction.

[Patent Document 1] JP-10-176065A (Claim 1)
[Patent Document 2] JP-60-13816A
[Patent Document 3] JP-61-9433A
[Patent Document 4] JP-9-165457A
[Patent Document 5] JP-7-70255A (Claim 1)

DISCLOSURE OF THE INVENTION

Problems to be Solved by the Invention

It is therefore an object of the present invention to provide a composition having a disperse system, which is capable of producing a multiple particle (e.g., multiple polymer particle) industrially with advantage by a convenient method even in the case where the multiple particle (e.g., a multiple polymer particle) comprises a plurality of organic solid materials (e.g., polymers), independent of (i) miscibility or immiscibility between a dispersed phase and a matrix, and (ii) solvent resistance; a process for producing a multiple particle from the composition having a disperse system; and the multiple particle.

It is another object of the present invention to provide a composition having a disperse system, which is applicable for various organic solid materials (e.g., polymers) irrespective of a polymerization method and is useful for producing a multiple particle (e.g., a multiple polymer particle) having a core-shell structure; a process for producing the multiple particle; and the multiple particle.

It is still another object of the present invention to provide a composition having a disperse system, which is stably capable of producing a multiple particle having a structure such as a core-shell structure even in a large particle size; a process for producing the multiple particle; and the multiple particle.

It is a further object of the present invention to provide a composition having a disperse system, which is capable of narrowing a particle size distribution and controlling (or adjusting) a particle size of a multiple particle, and useful for obtaining a spherical multiple particle; a process for producing the multiple particle; and the multiple particle.

It is a still further object of the present invention to provide a composition having a disperse system, which is capable of reducing the burden on the environment due to a waste fluid or other factors, and a process for producing a multiple particle from the composition.

Means to Solve the Problems

The inventor of the present invention made intensive studies to achieve the above objects and finally found that even in a plurality of organic solid materials (e.g., polymers), a particulate dispersed phase having a multiple (or composite) structure (e.g., a core-shell structure) can be stably formed by using, as a matrix of a composition having a disperse system, an auxiliary component comprising at least an oligosaccharide, and that a multiple particle (e.g., a multiple polymer particle) combining characteristics of a plurality of organic solid materials (e.g., polymers) can be obtained by further eluting or extracting the auxiliary component with an aqueous medium or the like. The present invention was accomplished based on the above findings.

That is, the multiple particle (or composite particle) of the present invention comprises an organic solid component (e.g., a polymer component) (A), and the organic solid component (A) comprises a plurality of organic solid materials each having a different affinity relative to a water-soluble auxiliary component (B) comprising at least an oligosaccharide (B1). The plurality of the organic solid materials (e.g., polymers) may form a polymer alloy. Moreover, the multiple particle may have a core-shell structure, wherein the core part (or core) contains a first organic solid material (e.g., a polymer) (A1) and the shell part (or shell) contains a second organic solid material (e.g., a polymer) (A2). In the core-shell structure, the shell may have a thickness of not more than 1 μm (for example, about 10 nm to 1 μm). At least one organic solid material (e.g., a polymer) of the plurality of the organic solid materials may be a polymer obtained by a non-addition polymerization (or a non-addition polymerization polymer). The organic solid component (A) may comprise a first organic solid material (e.g., a polymer) (A1) and a second organic solid material (e.g., a polymer) (A2) different in affinity relative to the auxiliary component (B) from each other. The ratio (weight ratio) of the first organic solid material (e.g., a polymer) (A1) relative to the second organic solid material (e.g., a polymer) (A2) [(A1)/(A2)] may be about 30/70 to 99/1, The organic solid component (A) may comprise a hydrophobic polymer (A1), and a hydrophilic polymer (A2) having at least one hydrophilic group selected from the group consisting of a hydroxyl group, a carboxyl group, an amino group, an imino group, an ether group, an oxyalkylene group, an ester group and an amide group. The hydrophilic polymer (A2) may contain at least one member selected from the group consisting of a vinyl acetate-series polymer (or resin), a polyvinyl alcohol-series polymer (or resin), a polyester-series polymer (or resin), a polyamide-series polymer (or resin), a polycarbonate-series polymer (or resin), a polyurethane-series polymer (or resin) and a cellulose derivative. The multiple particle may be a spherical particle, and the spherical particle may have an average particle size of 0.1 to 100 μm, a coefficient of variation of the average particle size of not more than 60, and a length ratio of a major axis relative to a minor axis of 1.5/1 to 1/1.

The present invention also includes a composition having a disperse system (or a dispersion composition), which comprises a matrix comprising a water-soluble auxiliary component (B) containing at least an oligosaccharide (B1), and a particulate dispersed phase comprising an organic solid component (A) containing a plurality of organic solid materials, and dispersed in the matrix. In the dispersion composition, the organic solid component (A) may comprise a first organic solid material (e.g., a polymer) (A1) having a lower affinity relative to the auxiliary component (B), and a second organic solid material (e.g., a polymer) (A2) having a higher affinity relative to the auxiliary component (B). The first organic solid material (A1) and the second organic solid material (A2) may be immiscible with each other.

The oligosaccharide (B1) may comprise at least a tetrasaccharide. The oligosaccharide (B1) may comprise at least one member selected from the group consisting of a starch sugar, a galactooligosaccharide, a coupling sugar, a fructooligoiaccharide, a xylooligosaccharide, a soybean oligosaccharide, a chitin oligosaccharide and a chitosan oligosaccharide. The oligosaccharide (B1) may have a viscosity of not lower than 1 Pa·s when a 50% by weight aqueous solution of the oligosaccharide is measured at a temperature of 25° C. by a B-type viscometer. The auxiliary component (B) may comprise the oligosaccharide (B1) and a water-soluble plasticizing component (B2) for plasticizing the oligosaccharide (B1). In the case of using the oligosaccharide (B1) and the plasticizing component (B2) in combination, the plasticizing component (B2) can effectively plasticize or soften the oligosaccharide (B1) even when the oligosaccharide (B1) is a thermally decomposable oligosaccharide. The oligosaccharide (B1) may show a melting point or softening point or may be decomposed (thermally decomposed) at a temperature (e.g., about 90 to 290° C.) higher than each of heat distortion temperatures of a plurality of organic solid materials (e.g., polymers) constituting the organic solid component (A), and the melting point or softening point of the plasticizing component (B2) may be not higher than the heat distortion temperature of at least one (e.g., a polymer) of the plurality of the organic solid materials. The plasticizing component (B2) may comprise at least one member selected from the group consisting of a saccharide (e.g., a monosaccharide, and a disaccharide) and a sugar alcohol (e.g., erythritol, pentaerythritol, arabitol, ribitol, xylitol, sorbitol, dulcitol and mannitol). The ratio (weight ratio) of the oligosaccharide (B1) relative to the plasticizing component (B2) [the oligosaccharide (B1)/the plasticizing component (B2)] may be about 99/1 to 50/50. In the dispersion composition, the organic solid component (A) may comprise a plurality of polymers, each of the polymers may have a Vicat softening temperatures defined by JIS K 7206 of 60 to 300° C., and the oligosaccharide (B1) may have a viscosity of 3 to 100 Pa·s when the viscosity is measured using a 50% by weight aqueous solution of the oligosaccharide at a temperature of 25° C. by a B-type viscometer. Moreover, the auxiliary component (B) comprising the oligosaccharide (B1) and the plasticizing component (B2) may have a melt flow rate defined by JIS K 7210 of not less than 1 when measured at a temperature 30° C. higher than the minimum point of the Vicat softening temperatures of the plurality of polymers. The ratio (weight ratio) of the organic solid component (A) relative to the auxiliary component (B) [the organic solid component (A)/the auxiliary component (B)] may be about 55/45 to 1/99.

The present invention further includes a process for producing a multiple particle (e.g., a multiple polymer particle) comprising an organic solid component (A) containing a plurality of organic solid materials (e.g., polymers), which comprises eluting an auxiliary component (B) from the dispersion composition.

Incidentally, in the present invention, the dispersion composition may be a polymer composition forming a disperse system containing an auxiliary component and an organic solid component comprising a plurality of organic solid materials, and the term "dispersion composition" is sometimes used synonymously with the term "polymer composition" accordingly. Moreover, in the present invention, an organic solid component comprising a plurality of organic solid materials, or a multiple (or composite) matter of a plurality of organic solid materials is sometimes simply referred to as "an organic solid component"; a polymer component comprising a plurality of polymers, or a multiple (or composite) matter of a plurality of polymers is sometimes simply referred to as "a polymer component"; and a water-soluble auxiliary component is sometimes simply referred to as "an auxiliary component". Incidentally, the term "spherical" shape is not limited to a finely spherical shape, and includes a shape having a length ratio of a major axis relative to a minor axis of about 1.5/1 to 1/1.

Throughout this description, the meaning of the term "organic solid component" includes not only a carbon-containing organic compound but also a silicon-containing compound (e.g., a silicone) as far as the compounds are in a solid form.

Effects of the Invention

According to the present invention, since a water-soluble auxiliary component comprising at least an oligosaccharide constitutes a matrix of a dispersion composition, even in a multiple particle comprising a plurality of organic solid materials, a multiple particle corresponding to the dispersed phase can be produced by a convenient method industrially with advantage independently of (i) affinity (miscibility or immiscibility) between a dispersed phase and a matrix, and (ii) solvent resistance. Moreover, the present invention can be applied to various polymers independent of the kind of polymerization method, and a multiple particle having a core-shell structure or other structure can be produced. Even when the particle size is large, the multiple particle having a core-shell structure can be stably produced. The present invention ensures to narrow the particle size distribution and control the particle size of the multiple polymer particle, and also ensures to obtain a spherical multiple particle. Further, since the water-soluble auxiliary component is derived from a natural product, the burden on the environment due to a waste fluid or other factors can be reduced.

DETAILED DESCRIPTION OF THE INVENTION

[Dispersion Composition]

In the dispersion composition of the present invention, a particulate dispersed phase comprising an organic solid component (A) containing a plurality of organic solid materials is dispersed in a matrix comprising a water-soluble auxiliary component (B) containing at least an oligosaccharide (B1).

(A) Meltable Organic Solid Component

The combination of a plurality of organic solid materials is not particularly limited to a specific one, and the materials may be organic solid materials (e.g., polymers) being miscible with each other, or may be organic solid materials (e.g., polymers) being immiscible with each other. In the dispersed phase (or multiple particle), for example, a plurality of organic solid materials (e.g., polymers) being miscible with each other may form a polymer alloy, or a plurality of organic solid materials (e.g., polymers) being immiscible with each other may form a phase separation structure [e.g., an islands-in-the-sea structure, a bicontinuous phase structure, and a core-shell structure (including a multi-layered core-shell structure)].

A plurality of organic solid materials constituting the organic solid component (A) may be combined by suitably selecting from the below-mentioned materials (low molecular weight compounds, and high molecular weight compounds).

As the meltable (or thermoplastic) organic solid component (A), a component (water-insoluble component) immiscible with or hydrophobic relative to the water-soluble auxiliary agent (or component) (B) may be usually employed. The organic solid component (A) is usually a solid at a room temperature (about 15 to 25° C.), and may be a low molecular weight compound or a high molecular weight compound (or a polymer or resin). The melting point of the organic solid component (A) having a low molecular weight may be about 40 to 280° C. (preferably about 50 to 270° C., and more preferably about 70 to 260° C.), or a compound having a relatively high melting point (about 100 to 260° C.) may be used as the organic solid component (A).

The organic solid component (A) having a low molecular weight may include, for example, a wax or lipid, a stabilizer (e.g., an antioxidant such as a hindered phenol-series, a hindered amine-series or a phosphorus-series antioxidant, and an ultraviolet ray absorbing agent or light stabilizer such as a benzophenone-series or a salicylic acid-series ultraviolet ray absorbing agent or a hindered amine-series light stabilizer), an antistatic agent, a flame retardant, a lubricant, a nucleation agent, a vulcanization accelerator, an antiaging agent, and a vulcanizing agent. Examples of the wax or lipid may include an aliphatic hydrocarbon-series wax (e.g., a polyolefinic wax such as a polyethylene wax or a polypropylene wax, a paraffin-series wax, and a microcrystalline wax), a plant- or animal-derived wax (e.g., a carnauba wax, a yellow bees wax, a shellac wax, and a montan wax), a higher fatty acid ester (e.g., a glycerin fatty acid ester, a diglycerin fatty acid ester, and a polyglycerin fatty acid ester), a fatty acid amide (e.g., stearic acid amide, and erucic acid amide), an alkylenebis fatty acid amide (e.g., methylenebisstearic acid amide, ethylenebisstearic acid amide, and ethylenebishydroxystearic acid amide), a metal salt of a fatty acid (e.g., a polyvalent metal salt of a higher fatty acid, such as barium laurate, zinc laurate, calcium stearate, zinc stearate or magnesium stearate). Incidentally, the wax or lipid may be also used as a lubricant. These components may be used singly or in combination.

According to the present invention, even in such an organic solid component having a low molecular weight, a particle (in particular a fine spherical particle) may be obtained by using in combination with the water-soluble auxiliary agent (B). Therefore, the present invention can improve in handleability of such an organic solid component (A) having a low molecular weight.

As the organic solid component (A), a high molecular weight compound (polymer or resin) is often used. Examples of the polymer may include a thermosetting resin [for example, an epoxy polymer, an unsaturated polyester polymer, a diallyl phthalate polymer, and a silicone (e.g., a silicone rubber, and a silicone varnish)], and usually include a thermoplastic resin, e.g., a condensation-series thermoplastic resin [for example, a polyester-series polymer (e.g., an aromatic polyester-series polymer, and an aliphatic polyester-series polymer), a polyamide-series polymer, a polyurethane-series polymer, a poly(thio)ether series polymer (e.g., a polyacetal-series polymer, a polyphenylene ether-series polymer, a polysulfide-series polymer, and a polyether ketone-series polymer), a polycarbonate-series polymer, a polysulfone-series polymer, and a polyimide-series polymer], a vinyl polymerization-type (or series) (additive polymerization-type (or series)) thermoplastic resin [for example, a polyolefinic polymer, a (meth)acrylic polymer, a styrenic polymer, and a vinyl-series polymer (e.g., a halogen-containing polymer, a vinyl ester-series polymer, and a vinyl alcohol-series polymer)], a natural product-derived polymer such as a cellulose derivative, and a thermoplastic silicone.

(1) Polyester-Series Polymer

The polyester-series polymer (or resin) may include, for example, a polyester including a copolyester obtained by a polycondensation of a dicarboxylic acid component and a diol component; a polyester including a copolyester obtained by a polycondensation of a hydroxycarboxylic acid; and a polyester including a copolyester obtained by a ring opening polymerization of a lactone. These polyester-series polymers may be used singly or in combination.

The dicarboxylic acid component may include, for example, an aromatic dicarboxylic acid [e.g., an aromatic dicarboxylic acid having about 8 to 20 carbon atoms, such as terephthalic acid, isophthalic acid, phthalic acid; an alkyl-substituted phthalic acid such as methylterephthalic acid or methylisophthalic acid; a naphthalenedicarboxylic acid (e.g., 2,6-naphthalenedicarboxylic acid, 2,7-naphthalenedicarboxylic acid, and 1,5-naphthalenedicarboxylic acid); a diphenyldicarboxylic acid such as 4,4'-diphenyldicarboxylic acid or 3,4'-diphenyl dicarboxylic acid; a diphenoxyethanedicarboxylic acid such as 4,4'-diphenoxyethanedicarboxylic acid; a diphenyl ether-dicarboxylic acid such as diphenyl ether-4, 4'-dicarboxylic acid; a diphenylalkanedicarboxylic acid such as diphenylmethanedicarboxylic acid or diphenylethanedicarboxylic acid; or a diphenylketonedicarboxylic acid], an aliphatic dicarboxylic acid (e.g., an aliphatic dicarboxylic acid having about 2 to 40 carbon atoms, such as oxalic acid, succinic acid, adipic acid, azelaic acid, sebacic acid, dodecanedioic acid, hexadecanedicarboxylic acid, or dimeric acid), and an alicyclic dicarboxylic acid (e.g., an alicyclic dicarboxylic acid having about 8 to 12 carbon atoms, such as cyclohexanedicarboxylic acid, hexahydrophthalic acid, hexahydroisophthalic acid, hexahydroterephthalic acid, or himic acid). These dicarboxylic acid components may be used singly or in combination.

Incidentally, the dicarboxylic acid component may also include an ester-formable derivative, e.g., a lower alkyl ester such as a dimethyl ester, an acid anhydride, and an acid halide such as an acid chloride.

Examples of the diol component may include an aliphatic $C_{2-12}$ diol (e.g., ethylene glycol, propylene glycol, 1,4-butanediol, 1,3-butanediol, neopentyl glycol, hexanediol, and a (poly)$C_{2-4}$alkylene glycol (e.g., diethylene glycol and dipropylene glycol)); and an alicyclic $C_{6-12}$ diol (e.g., cyclohexanediol, and cyclohexanedimethanol); an aromatic $C_{6-20}$ diol (e.g., resorcinol, hydroquinone, naphthalenediol, a bisphenol compound such as bisphenol A, F, or AD; and an adduct of a bisphenol compound with an alkylene oxide). These diol components may be used singly or in combination.

The hydroxycarboxylic acid may include, for example, an aliphatic $C_{2-6}$hydroxycarboxylic acid such as glycolic acid, lactic acid, hydroxypropionic acid, hydroxybutyric acid, glyceric acid, or tartronic acid; and an aromatic hydroxycarboxylic acid such as hydroxybenzoic acid, or hydroxynaphthoic acid. These hydroxycarboxylic acids may be used singly or in combination.

Examples of the lactone may include a $C_{3-12}$lactone such as propiolactone, butyrolactone, valerolactone, or caprolactone. These lactones may be used singly or in combination. Among these lactones, a $C_{4-10}$lactone, in particular a caprolactone (e.g., ε-caprolactone), is preferred.

The polyester-series polymer may include an aromatic polyester-series polymer, an aliphatic polyester-series polymer, and others.

Examples of the aromatic polyester-series polymer may include a polyester including a copolyester obtained by polycondensation of the aromatic dicarboxylic acid (preferably, an aromatic dicarboxylic acid having about 8 to 20 carbon atoms, such as terephthalic acid, isophthalic acid, phthalic acid or a naphthalenedicarboxylic acid) and the aliphatic diol (preferably, e.g., an aliphatic $C_{2-12}$diol such as ethylene glycol, propylene glycol, 1,4-butanediol or 1,3-butanediol) or the alicyclic diol (preferably, an alicyclic $C_{6-20}$diol such as cyclohexanedimethanol), and preferably include a polyester including a copolyester having an alkylene arylate unit such as an alkylene terephthalate or in alkylene naphthalate as a main unit (e.g., not less than 50% by weight). The copolymerizable component may include a polyC$_{2-4}$alkylene glycol having a repeating oxyalkylene unit of about 2 to 4 [e.g., a glycol compound containing a poly(oxy-C$_{2-4}$alkylene) unit such as diethylene glycol], or an aliphatic dicarboxylic acid having about 6 to 12 carbon atoms (e.g., adipic acid, pimelic acid, suberic acid, azelaic acid, and sebacic acid).

More specifically, as the aromatic polyester-series polymer, there may be exemplified a polyalkylene terephthalate [e.g., a polycycloalkanediC$_{1-4}$alkylene terephthalate such as a poly(1,4-cyclohexanedimethylene terephthalate) (PCT); and a polyC$_{2-4}$alkylene terephthalate such as a polyethylene terephthalate (PET) or a polybutylene terephthalate (PBT)], a polyC$_{2-4}$alkylene naphthalate corresponding to the polyalkylene terephthalate (e.g., a polyethylene naphthalate), a polyethylene terephthalate copolyester containing an ethylene terephthalate unit as a main unit, and a polybutylene terephthalate copolyester containing a butylene terephthalate unit as a main unit. The aromatic polyester-series polymer may be a liquid crystalline polyester.

Examples of the aliphatic polyester-series polymer may include a polyester including a copolyester obtained by a polycondensation of the aliphatic dicarboxylic acid component (e.g., an aliphatic dicarboxylic acid having about 2 to 6 carbon atoms, such as oxalic acid, succinic acid or adipic acid, and preferably an aliphatic dicarboxylic acid having about 2 to 4 carbon atoms, such as oxalic acid or succinic acid) and the aliphatic diol component (e.g., an aliphatic C$_{2-6}$diol (a C$_{2-6}$alkanediol) such as ethylene glycol, propylene glycol, 1,4-butanediol, 1,3-butanediol, neopentyl glycol or hexanediol, and preferably an aliphatic C$_{2-4}$diol (a C$_{2-4}$alkanediol) such as ethylene glycol, 1,4-butanediol or neopentyl glycol), a polyester including a copolyester of the aliphatic hydroxycarboxylic acid (e.g., an aliphatic C$_{2-6}$hydroxycarboxylic acid such as glycolic acid, lactic acid, hydroxypropionic acid or hydroxybutyric acid, and preferably an aliphatic C$_{2-4}$hydroxycarboxylic acid such as glycolic acid or lactic acid), and a homopolylactone or copolylactone obtained by a ring opening polymerization of the lactone (preferably, a C$_{4-10}$lactone such as caprolactone) with an initiator (a bifunctional or trifunctional initiator, e.g., an active hydrogen-containing compound such as an alcohol compound). The copolymerizable component may include a polyC$_{2-4}$alkylene glycol having a repeating oxyalkylene unit of about 2 to 4 [e.g., a glycol compound containing a poly(oxy-C$_{2-4}$alkylene) unit such as diethylene glycol], or an aliphatic dicarboxylic acid having about 6 to 12 carbon atoms (e.g., adipic acid, pimelic acid, suberic acid, azelaic acid, and sebacic acid).

More specifically, the aliphatic polyester-series polymer may include, for example, a polyester-series polymer obtained by a polycondensation of a dicarboxylic acid component and a diol component (for example, a polyC$_{2-6}$alkylene oxalate such as a polyethylene oxalate, a polybutylene oxalate or a polyneopentylene oxalate; a polyC$_{2-6}$alkylene succinate such as a polyethylene succinate, a polybutylene succinate or a polyneopentylene succinate; and a polyC$_{2-6}$alkylene adipate such as a polyethylene adipate, a polybutylene adipate or a polyneopentylene adipate), a polyhydroxycarboxylic acid-series polymer (e.g., a homo- or copolymer of a hydroxyC$_{2-10}$alkanecarboxylic acid, such as a polyglycolic acid, a polylactic acid, or a lactic acid-glycolic acid copolymer), and a polylactone-series polymer [e.g., a poly C$_{3-12}$ lactone-series polymer such as a polycaprolactone (e.g., "PCLH7", "PCLH4" and "PCLH1" manufactured by Daicel Chemical Industries, Ltd.)]. The concrete examples of the copolyester include a copolyester containing two kinds of dicarboxylic acid components (e.g., a polyC$_{2-4}$alkylene succinate-adipate copolymer such as a polyethylene succinate-adipate copolymer or a polybutylene succinate-adipate copolymer), and a copolyester obtained from a dicarboxylic acid component, a diol component and a lactone (e.g., a polycaprolactone-polybutylene succinate copolymer).

The polyester-series polymer used in the present invention may be a polyester-series polymer containing a urethane bond (for example, an aliphatic polyester-series polymer containing a urethane bond). The polyester-series polymer containing a urethane bond preferably includes a polymer obtained by allowing the above polyester-series polymer (e.g., a polyester diol having a low molecular weight) to have a high molecular weight with a diisocyanate compound (e.g., an aliphatic diisocyanate).

The diisocyanate compound may include an aromatic diisocyanate (e.g., a phenylene diisocyanate, a tolylene diisocyanate, and diphenylmethane-4,4'-diisocyanate), an araliphatic diisocyanate compound (e.g., a xylylene diisocyanate), an alicyclic diisocyanate compound (e.g., isophorone diisocyanate), an aliphatic diisocyanate compound (e.g., trimethylene diisocyanate, tetramethylene diisocyanate, pentamethylene diisocyanate, hexamethylene diisocyanate, lysine diisocyanatemethyl ester, and trimethylhexamethylene diisocyanate), and others. These diisocyanate compounds may be used singly or in combination. Among these diisocyanate compounds, the aliphatic diisocyanate compound, e.g., hexamethylene diisocyanate, may be used.

Examples of the polyester-series polymer containing a urethane bond (e.g., an aliphatic polyester-series polymer) may include "BIONOLLE #1000" series, "BIONOLLE #3000" series and "BIONOLLE #6000" series manufactured by Showa Highpolymer Co., Ltd.

(2) Polyamide-Series Polymer

The polyamide-series polymer (or resin) may include, for example, an aliphatic polyamide-series polymer, an alicyclic polyamide-series polymer, and an aromatic polyamide-series polymer, and the aliphatic polyamide-series polymer is usually employed. These polyamide-series polymers may be used singly or in combination.

Examples of the aliphatic polyamide-series polymer may include a condensate (or condensed product) of an aliphatic diamine component (a C$_{4-10}$alkylenediamine such as tetramethylenediamine or hexamethylenediamine) and an aliphatic dicarboxylic acid component (e.g., a C$_{4-20}$alkylenedicarboxylic acid such as adipic acid, sebacic acid or dodecanedioic acid) (for example, a polyamide 46, a polyamide 66, a polyamide 610, a polyamide 612, a polyamide 1010, a polyamide 1012, and a polyamide 1212), a homo- or copolymer of a lactam (e.g., a C$_{4-20}$lactam such as ε-caprolactam or ω-laurolactam) or an aminocarboxylic acid (e.g., a C$_{4-20}$aminocarboxylic acid such as ω-aminoundecanoic acid) (for example, a polyamide 6, a polyamide 11, a polyamide 12, a polyamide 6/11, and a polyamide 6/12); and a copolyamide having these polyamide components copolymerized therein (for example, a polyamide 66/11, and a polyamide 66/12).

Further, the polyamide-series polymer may have biodegradability. The biodegradable polyamide-series polymer may include a polyester amide as a condensate of the aliphatic diamine component (a C$_{4-10}$alkylenediamine such as tetramethylenediamine or hexamethylenediamine), the aliphatic dicarboxylic acid component (e.g., a C$_{4-20}$alkylenedicarboxylic acid such as adipic acid, sebacic acid or dodecanedioic acid) and the aliphatic diol component (e.g., a C$_{2-12}$alkylene glycol such as ethylene glycol, propylene glycol or butanediol).

(3) Polyurethane-Series Polymer

The polyurethane-series polymer (or resin) may be obtained by a reaction between a diisocyanate compound and a polyol compound (e.g., a diol compound) and, if necessary, a chain-extension agent. As the diisocyanate compound, there may be exemplified an aliphatic diisocyanate compound such as hexamethylene diisocyanate or 2,2,4-trimethylhexamethylene diisocyanate; an alicyclic diisocyanate compound such as 1,4-cyclohexane diisocyanate or isophorone diisocyanate; an aromatic diisocyanate compound such as a phenylene diisocyanate, a tolylene diisocyanate, diphenylmethane-4,4'-diisocyanate or 1,5-naphthalene diisocyanate; an araliphatic diisocyanate compound such as a xylylene diisocyanate; and others.

The polyol compound may include, for example, a polyester polyol, a polyether polyol, and a polycarbonate polyol. Among the polyol compounds, a diol compound (e.g., a polyester diol, a polyether diol, and a polycarbonate diol) is particularly preferred. These polyol compounds may be used singly or in combination.

Examples of a compound available as the diol compound may include a polyester diol (e.g., a polyester diol derived from a $C_{4-12}$aliphatic dicarboxylic acid component such as succinic acid, adipic acid or azelaic acid, and a $C_{2-12}$aliphatic diol component such as ethylene glycol, propylene glycol, butanediol or neopentyl glycol; a polyester diol derived from a $C_{4-12}$lactone component such as ε-caprolactone; and a polyester diol derived from the aliphatic dicarboxylic acid component and/or the aliphatic diol component, and the lactone component), a polyether diol (e.g., a polyethylene glycol, a polypropylene glycol, a polyoxyethylene-polyoxypropylene block copolymer, a polytetramethylene glycol, and a bisphenol A-alkylene oxide adduct), and a polyester ether diol (e.g., a polyester diol obtained by using the polyether diol as part of a diol component).

Further, as the chain-extension agent, there may be used a $C_{2-10}$alkylene glycol such as ethylene glycol or propylene glycol, and in addition, a diamine compound [for example, an aliphatic diamine compound (a linear or branched alkylenediamine such as ethylenediamine, trimethylenediamine or tetramethylenediamine; and a linear or branched polyalkylenepolyamine such as diethylenetriamine, triethylenetetramine, tetraethylenepentamine or dipropylenetriamine), an alicyclic diamine compound (e.g., isophoronediamine), and an aromatic diamine compound (e.g., phenylenediamine, and xylylenediamine)]. These polyurethane-series polymers may be used singly or in combination.

(4) Poly(Thio)Ether-Series Polymer

Examples of the poly(thio)ether-series polymer (or resin) may include a polyalkylene glycol, a polyphenylene ether-series polymer, and a polysulfide-series polymer (polythioether-series polymer). The polyalkylene glycol may include a homo- or copolymer of an alkylene glycol (e.g., a poly$C_{2-4}$alkylene glycol) such as a polypropylene glycol, a polytetramethylene ether glycol, or a polyoxyethylene-polyoxypropylene block copolymer. These poly(thio)ether-series polymers may be used singly or in combination.

(5) Polycarbonate-Series Polymer

The polycarbonate-series polymer (or resin) may include, for example, an aromatic polycarbonate containing a bisphenol compound (e.g., bisphenol A) as a base unit, and an aliphatic polycarbonate such as diethylene glycol bisallyl carbonate. These polycarbonate-series polymers may be used singly or in combination.

(6) Polysulfone-Series Polymer

Examples of the polysulfone-series polymer (or resin) may include a polysulfone polymer obtained by polycondensation of a dihalogenodiphenyl sulfone (e.g., dichlorodiphenyl sulfone) and a bisphenol compound (e.g., bisphenol A or a metal salt thereof), a polyether sulfone polymer, and a polyallyl sulfone polymer (brand name: RADEL). These polysulfone-series polymers may be used singly or in combination.

(7) Polyolefinic Polymer

The polyolefinic polymer (or resin) may include a homo- or copolymer of an α-$C_{2-6}$olefin, for example, a homo- or copolymer of an olefin such as a polyethylene, a polypropylene, an ethylene-propylene copolymer or a poly(methylpentene-1), and a copolymer of an olefin and a copolymerizable monomer (e.g., an ethylene-vinyl acetate copolymer, an ethylene-(meth)acrylic acid copolymer, and an ethylene-(meth) acrylate copolymer). These polyolefinic polymers may be used singly or in combination.

(8) (Meth)Acrylic Polymer

As the (meth)acrylic polymer (or resin), there may be mentioned a homo- or copolymer of a (meth)acrylic monomer [e.g., (meth)acrylic acid, a $C_{1-18}$alkyl(meth)acrylate, a hydroxyalkyl (meth)acrylate, a glycidyl(meth)acrylate, and (meth)acrylonitrile], for example, a poly(meth)acrylate such as a poly(methyl(meth)acrylate), a methyl methacrylate-(meth)acrylic acid copolymer, a methyl methacrylate-acrylate-(meth)acrylic acid copolymer, a methyl methacrylate-(meth)acrylate copolymer, and a (meth)acrylate-styrene copolymer (e.g., an MS polymer). The preferred (meth)acrylic polymer includes a poly($C_{1-5}$alkyl(meth)acrylate), a methyl methacrylate-acrylate copolymer, a (meth)acrylate-styrene copolymer (e.g., an MS polymer), and others. These (meth)acrylic polymers may be used singly or in combination.

(9) Styrenic Polymer

Examples of the styrenic polymer (or resin) may include a homo- or copolymer of a styrenic monomer (e.g., styrene, α-methylstyrene, and vinyl toluene) (for example, a polystyrene, a styrene-vinyl toluene copolymer, and a styrene-α-methylstyrene copolymer), a copolymer of a styrenic monomer and copolymerizable monomer(s) [for example, a copolymer such as a styrene-acrylonitrile copolymer (an AS polymer), a (meth)acrylate-styrene copolymer (e.g., an MS polymer), a styrene-maleic anhydride copolymer, or a styrene-butadiene block copolymer; a styrenic graft copolymer such as an acrylonitrile-acrylate-styrene copolymer (an AAS polymer), an acrylonitrile-chlorinated polyethylene-styrene copolymer (an ACS polymer), or an acrylonitrile-vinyl acetate-styrene copolymer (e.g., an AXS polymer); and a graft polymer obtained by a graft polymerization of at least a styrenic monomer in the presence of a rubber component, for example, a high impact polystyrene (HIPS, or a rubber-grafted polystyrenic polymer), an acrylonitrile-butadiene-styrene copolymer (an ABS polymer), and an acrylonitrile-ethylene propylene rubber-styrene copolymer (an AES polymer)]. These styrenic polymers may be used singly in combination.

(10) Vinyl-Series Polymer

Examples of the vinyl-series polymer (or resin) may include a homo- or copolymer of a vinyl-series monomer, or a copolymer of a vinyl-series monomer and other copolymerizable monomer(s). The vinyl-series monomer may include, for example, a halogen-containing vinyl monomer [for example, a chlorine atom-containing vinyl monomer (e.g., vinyl chloride, vinylidene chloride, and chloroprene), and a fluorine atom-containing vinyl monomer (e.g., fluoroethylene)], and a vinyl carboxylate [for example, a vinyl ester such as vinyl acetate, vinyl propionate, vinyl crotonate or vinyl benzoate]. These vinyl-series polymers may be used singly or in combination.

As the vinyl-series polymer, for example, there may be mentioned a vinyl chloride-series polymer (e.g., a polyvinyl chloride, a polyvinylidene chloride, a vinyl chloride-vinyl acetate copolymer, and a vinylidene chloride-vinyl acetate copolymer), a fluorocarbon polymer (e.g., a polyvinyl fluoride, a polyvinylidene fluoride, a polychlorotrifluoroethylene, a tetrafluoroethylene-hexafluoropropylene copolymer, a tetrafluoroethylene-perfluoroalkyl vinyl ether copolymer, and a tetrafluoroethylene-ethylene copolymer), and a vinyl ester-series polymer (e.g., a polyvinyl acetate; a vinyl acetate-series copolymer such as an ethylene-vinyl acetate copolymer, a vinyl acetate-vinyl chloride copolymer, or a vinyl acetate-(meth)acrylate copolymer).

Moreover, the vinyl-series polymer may also include a derivative of the vinyl ester-series polymer, for example, a vinyl alcohol-series polymer (e.g., a polyvinyl acetal such as a polyvinyl formal or a polyvinyl butyral; and a saponification product of the vinyl acetate-series copolymer, e.g., an ethylene-vinyl alcohol copolymer). Among these vinyl alcohol-series polymers, the saponification product of the vinyl acetate-series copolymer, in particular the ethylene-vinyl alcohol copolymer, is preferred. In the saponification product of the vinyl acetate-series copolymer, the degree of hydrophilicity may be controlled by adjusting a proportion of a hydrophobic comonomer unit (e.g., an ethylene unit in an ethylene-vinyl alcohol copolymer). In the case of using the saponification product of the vinyl acetate-series copolymer as a hydrophilic polymer, the proportion of the hydrophobic monomer unit may be adjusted to, for example, about 10 to 40% by weight from the viewpoint of affinity relative to the auxiliary component (B).

(11) Cellulose Derivative

Examples of the cellulose derivative may include a cellulose ester compound (e.g., a cellulose acetate, and a cellulose phthalate), a cellulose carbamate compound (e.g., a cellulose phenylcarbamate), and a cellulose ether compound (e.g., a cyanoethyl cellulose). These cellulose derivatives may be used singly or in combination.

As the cellulose ester, for example, there may be mentioned an organic acid ester of a cellulose (or an acyl cellulose), e.g., a cellulose acetate (an acetyl cellulose) such as a cellulose diacetate or a cellulose triacetate, a cellulose propionate, a cellulose butyrate, a cellulose acetate propionate, and a cellulose acetate butyrate; an inorganic acid ester of a cellulose such as a cellulose nitrate, a cellulose sulfate or a cellulose phosphate; and a mixed acid ester of a cellulose such as a cellulose nitrate acetate.

The cellulose ether may include, for example, an alkyl cellulose (e.g., a $C_{2-6}$alkyl cellulose such as an ethyl cellulose, an isopropyl cellulose or a butyl cellulose), an aralkyl cellulose (e.g., a benzyl cellulose), and a cyanoethyl cellulose.

In view of biodegradability, it is preferred that the substitution degree of the cellulose derivative is low. For example, the average substitution degree is not more than 2.5, preferably not more than 2 (e.g., about 0.1 to 2), and more preferably not more than 1.5 (e.g., about 0.1 to 1.5).

(12) Thermoplastic Elastomer

Examples of the thermoplastic elastomer may include a polyamide-series elastomer [for example, a block copolymer comprising a polyamide block (e.g., an aliphatic polyamide) as a hard segment part and a polyether or polyester block having a low glass transition temperature (e.g., an ether block such as a polyoxy$C_{2-4}$alkylene block such as a polyoxytetramethylene or polyoxypropylene block; and an aliphatic polyester block) as a soft segment part], a polyester-series elastomer [for example, a block copolymer comprising a polyester block (e.g., an aromatic crystalline polyester such as a polybutylene terephthalate, and a liquid crystal polyester) as a hard segment part and the polyether or polyester block as a soft segment part], a polyurethane-series elastomer [for example, a block copolymer comprising a polyurethane block as a hard segment part and the polyether or polyester block as a soft segment part], a polystyrenic elastomer [for example, a block copolymer comprising a polystyrene block and a diene or olefin block, e.g., a styrene-butadiene-styrene (SBS) block copolymer, a styrene-isoprene-styrene (SIS) block copolymer, a styrene-ethylene-butylene-styrene block copolymer (SEBS), a styrene-ethylenepropylene-styrene block copolymer (SEPS), and a hydrogenated product of a random styrene-butadiene rubber (HSBR)], a polyolefinic elastomer [for example, a polyolefin (e.g., a polyethylene, and a polypropylene) as a hard segment part and a rubber component (e.g., a blend comprising an ethylene-propylene rubber (EPR), and an ethylene-propylene-diene rubber (EPDM)) as a soft segment part], a polydiene-series elastomer (for example, a syndiotactic 1,2-polybutadiene-series elastomer, a trans 1,4-polyisoprene-series elastomer, and a natural rubber-series elastomer), a chlorine-series elastomer [for example, a blend-formed elastomer comprising a highly polymerized or partially crosslinked polyvinyl chloride (hard segment part) and a polyvinyl chloride plasticized with a plasticizer (soft segment part), a polyvinyl chloride-series elastomer such as a polymer alloy-formed elastomer comprising a vinyl chloride polymer (hard segment part) and a rubber or elastomer component (e.g., a soft segment part such as a partially crosslinked nitrile rubber, a polyurethane-series elastomer, or a polyester-series elastomer); and a chlorinated polyethylene], and a fluorine-containing thermoplastic elastomer [for example, an ABA block copolymer comprising a fluorocarbon polymer (e.g., a tetrafluoroethylene-ethylene copolymer, and a polyvinylidene fluoride (PVDF)) as a hard segment part and a fluorine rubber (e.g., a vinylidene fluoride-hexafluoropropylene-tetrafluoroethylene ternary copolymer) as a soft segment part]. Incidentally, in the case where the thermoplastic elastomer is a block copolymer, the block structure is not particularly limited to a specific one, and may be a triblock structure, a multiblock structure, a star-shaped block structure, and others.

The heat distortion temperature of the polymer or resin (e.g., a Vicat softening temperature defined by JIS K 7206) may be selected from the range of 60 to 300° C., and for example, may be about 80 to 260° C., preferably about 100 to 240° C. (e.g., about 110 to 240° C.), and more preferably about 120 to 230° C. (e.g., about 130 to 220° C.).

A plurality of organic solid materials (e.g., polymers) constituting the organic solid component (A) may be suitably selected from the above-mentioned organic solid material (e.g., a low molecular weight compound, and a high molecular weight compound), and for example, may comprise 2 to 5 kinds, preferably 2 to 3 kinds (e.g., 2 kinds) of the organic solid materials.

In the present invention, a dispersion composition or multiple polymer particle can be obtained by even using a polymer derived from an addition-polymerizable monomer without limiting the way of polymerization of the polymer, and a multiple polymer particle having a structure such as a core-shell structure can be obtained even in the case of using a polymer obtained by not a seeded polymerization but a non-addition polymerization.

A plurality of organic solid materials constituting the organic solid component (A) may have a different affinity from each other relative to the water-soluble auxiliary component (B). Among a plurality of the organic solid materials constituting the organic solid component (A), at least one organic solid material may be an organic solid material (e.g., a hydrophilic polymer) having a high affinity relative to the auxiliary component. Along with formation of the dispersion composition, the organic solid material (e.g., a polymer) such as a hydrophilic polymer having a high affinity relative to the auxiliary component tends to be located in the neighborhood of the matrix in the dispersion composition, that is, outside or outer layer of the dispersed phase.

Therefore, in the case where an organic solid material (A2) having a higher affinity relative to the auxiliary component (B) (e.g., an affinity polymer or a hydrophilic polymer) and an organic solid material (A1) having a lower affinity relative to the component (B) (e.g., a non-affinity polymer or a hydrophobic polymer, a polymer having a lower affinity or hydrophilicity than the polymer (A2), and a wax or lipid) are combined, a dispersed phase (or a polymer particle) having a core-shell structure may be formed which comprises a core including the organic solid material (e.g., a polymer) (A1) and a shell covering the core and including the organic solid material (A2). In such a combination of the organic solid materials, as the miscibility between the organic solid materials (A1) and (A2) is decreased (that is, immiscibility is increased), a dispersed phase (or particle) having clearer boundary between the core and the shell can be formed. That is, depending on the miscibility between both materials (e.g., polymers), the core of the dispersed phase may be formed by the organic solid material (A1) alone, or by a mixture of the organic solid material (A1) and the organic solid material (A2), or others. Incidentally, in the case of selecting a combination of organic solid materials (e.g., polymers) having a high miscibility with each other as a plurality of organic solid materials, a polymer alloyed dispersed phase (or particle) can be obtained.

In the case where the dispersed phase (or multiple particle) has a core-shell structure, the internal property and the surface property of the disperse phase (or multiple particle) can be controlled by suitably selecting the kind of the organic solid material (e.g., a polymer) constituting the core and the kind of the organic solid material (e.g., a polymer) constituting the shell, and various functions can be imparted to a desired layer (the core or the shell) for any purpose. For example, the core may comprise a polymer excellent in a mechanical property (such as hardness) and the shell may comprise a polymer excellent in a surface property (such as a sliding property or an antistatic property), or heat weldability can be imparted to only the shell. In addition, a multiple particle (e.g., a multiple polymer particle) capable of effectively expressing properties or physical properties of the organic solid material (e.g., a polymer) can be obtained.

In a preferred embodiment, the organic solid component (A) may comprise (A1) a first organic solid material (or composition) having a lower affinity relative to the component (B), and (A2) a second organic solid material (or composition) having a higher affinity relative to the component (B). Examples of the material (A1) may include a polymer having no affinity (e.g., a hydrophobic or water-insoluble polymer), and a polymer having a lower affinity or hydrophilicity compared with the polymer (A2) (such a polymer having a lower affinity or hydrophilicity may be a hydrophilic polymer). Examples of the material (A2) may include a polymer having an affinity, or a hydrophilic polymer. The first organic solid material (e.g., a polymer) (A1) and the second organic solid material (e.g., a polymer) (A2) may be miscible with each other, or immiscible with each other. In such a combination, the dispersed phase may have a core-shell structure comprising a core containing the first organic solid material (e.g., a polymer) (A1) and a shell containing the second organic solid material (e.g., a polymer) (A2).

The polymer having an affinity (or the hydrophilic polymer) has a polar group, usually, a hydrophilic group (or a polar group) such as a hydroxyl group, a carboxyl group, an amino group, an imino group (—NH), an ether group, an oxyalkylene group (e.g., a linear or branched polyoxy$C_{2-4}$alkylene group such as a polyoxyethylene group or a polyoxypropylene group), an ester group (or ester linkage), an amide group (or amide linkage), or a urethane linkage (—NHC(=O)O—). The polymer having an affinity may have the single polar group, or not less than two kinds of the polar group.

Such a polymer having an affinity may include, among the above-mentioned polymers, for example, a hydrophilic polymer such as the vinyl acetate-series polymer, the polyvinyl alcohol-series polymer, the polyester-series polymer, the polyamide-series polymer, the polycarbonate-series polymer, the polyurethane-series polymer, the (meth)acrylic polymer [for example, a (meth)acrylic polymer having (meth)acrylic acid or an alkyl(meth)acrylate as a constitutional unit], the cellulose derivative, or the thermoplastic elastomer (e.g., a polyamide elastomer having a poly$C_{2-4}$oxyalkylene unit as a soft segment part, a polyester elastomer, and a polyurethane elastomer). These hydrophilic polymers may be used singly or in combination.

Among the combinations of the first and the second organic solid materials, a combination of the first polymer and the second polymer may include (a) a combination of different polymers, for example, a combination of a hydrophobic polymer (A1) and a hydrophilic polymer (A2), and (b) a combination of the same series polymers, and others. The combination of the same series polymers includes, for example, a (combination of polymers different in concentration of a polar group (such as a hydrophilic group) from each other. Moreover, the combination of the first polymer and the second polymer may be a combination of a hydrophilic polymer (A2) having a hydrophilic group having a higher hydrophilicity (e.g., a water-soluble group such as a carboxyl group, an amino group or an imino group) and a hydrophilic polymer (A1) having a hydrophilic group having a lower hydrophilicity (e.g., a hydroxyl group, an ether group, an oxyalkylene group, an ester group, an amide group, and a urethane linkage), and other combination. Among the first polymers (A1), examples of the hydrophobic polymer may include the polyolefinic polymer, the styrenic polymer, the hydrophobic vinyl-series polymer (e.g., a vinyl chloride-series polymer, and a fluororesin), and the thermoplastic elastomer (e.g., an olefinic elastomer, and a styrenic elastomer) among the above-mentioned thermoplastic resins. The hydrophobic polymer may be a polymer having a nonpolar group. These hydrophobic polymers may be also used singly or in combination.

Among the combinations of the first polymer and the second polymer, the combination (a) may include a combination of an olefinic elastomer or a styrenic elastomer (A1) with a polyamide-series polymer, a polyester-series polymer, a polyamide-series elastomer, a polyester-series elastomer or a polyurethane-series elastomer (A2), and other combination. Moreover, the combination (b) may include, for example, a combination of an aliphatic polyester-series polymer (A1) [e.g., a copolyester such as a poly$C_{2-4}$alkylene succinate-adipate copolymer; and a copolyester obtained from a dicarboxylic acid component, a diol component and a lactone (e.g., a polycaprolactone-polybutylene succinate copolymer)] and a homo- or copolyester (A2) of a short-chained hydroxycarboxylic acid or a lactone (e.g., a polylactic acid).

Moreover, in the case where the organic solid component (A) comprises a biodegradable polymer [for example, a biodegradable polyester-series polymer such as an aliphatic polyester-series polymer (e.g., a polylactic acid-series polymer, and a polyC$_{3-12}$lactone-series polymer) or a polyester amide, a vinyl alcohol-series polymer, and the above-mentioned cellulose derivative], a polymer particle excellent in biodegradability can be also obtained.

In the average molecular weight of each polymer constituting the polymer component, the weight-average molecular weight or the viscosity-average molecular weight may be, for example, not more than 500,000 (e.g., about 10,000 to 500,000), preferably about 50,000 to 400,000 and more preferably about 10,000 to 350,000, in terms of polystyrene by a gel-permeation chromatography. Incidentally, with respect to a thermoplastic resin (such as a cellulose derivative) with difficulty in molecular weight measurement by a gel-permeation chromatography, the viscosity-average molecular weight may be adopted. Incidentally, the weight-average molecular weight of the polymer component (A) may be also adjusted depending on a kneading time or a kneading temperature of the polymer component.

In the organic solid component (A), the ratio (weight ratio) of the first organic solid material (A1) relative to the second organic solid (A2) may be, for example, about 30/70 to 99/1, preferably about 40/60 to 95/5, and more preferably about 45/55 to 90/10 (e.g., about 50/50 to 90/10).

Incidentally, to the organic solid component (e.g., a polymer component) (A) may be added a compatibilizing agent as far as formation of the dispersed phase is not inhibited.

(B) Water-Soluble Auxiliary Component

The water-soluble auxiliary component comprises at least an oligosaccharide (B1). Moreover, in order to adjust a thermal fusing property of the oligosaccharide, the water-soluble auxiliary component may further comprise a plasticizing component (B2) for plasticizing the oligosaccharide. By using the oligosaccharide (B1) and the water-soluble plasticizing component (B2) in combination, the viscosity of the water-soluble auxiliary component (B) can be adjusted in kneading with the organic solid component (A). Incidentally, the multiple particle (e.g., a multiple polymer particle) may be obtained by forming a dispersion composition by using the water-soluble auxiliary component in combination with the organic solid component, and then suitably eluting or washing the water-soluble auxiliary component from the dispersion composition.

(B1) Oligosaccharide

The oligosaccharide (B1) is classified broadly into two groups: a homooligosaccharide condensed by dehydration of 2 to 10 monosaccharide molecules through glycoside linkage(s), and a heterooligosaccharide condensed by dehydration of 2 to 10 molecules of at least not less than two kinds of monosaccharides and/or sugar alcohols through glycoside linkage(s). The oligosaccharide (B1) may include, for example, a disaccharide to a decasaccharide, and usually, an oligosaccharide of a disaccharide to a hexasaccharide is employed. The oligosaccharide is usually a solid at a room temperature. Incidentally, these oligosaccharides may be an anhydrate. Moreover, in the oligosaccharide, a monosaccharide may bond (or link) with a sugar alcohol. Incidentally, the oligosaccharide may be an oligosaccharide composition comprising a plurality of sugar components. Such an oligosaccharide composition is sometimes simply referred to as an oligosaccharide. These oligosaccharides (or oligosaccharide compositions) may be used singly or in combination.

Examples of the disaccharide may include a homooligosaccharide such as a trehalose (e.g., α,α-trehalose, β,β-trehalose, and α,β-trehalose), kojibiose, nigerose, maltose, isomaltose, sophorose, laminaribiose, cellobiose or gentiobiose; and a heterooligosaccharide such as lactose, sucrose, palatinose, melibiose, rutinose, primeverose or ruranose.

As the trisaccharide, there may be mentioned a homooligosaccharide such as maltotriose, isomaltotriose, panose or cellotriose; a heterooligosaccharide such as manninotriose, solatriose, melezitose, planteose, gentianose, umbelliferose, lactosucrose or raffinose; and others.

Examples of the tetrasaccharide may include a homooligosaccharide such as maltotetraose or isomaltotetraose; and a heterooligosaccharide such as stachyose, cellotetraose, scorodose, lychnose, or a tetraose having a sugar or sugar alcohol attached to a reducing end of panose.

Among these tetrasaccharides, the tetraose having a monosaccharide or sugar alcohol attached to a reducing end of panose is disclosed in, for example, Japanese Patent Application Laid-Open No. 215892/1998 (JP-10-215892A), and may include a tetraose having a monosaccharide (such as glucose, fructose, mannose, xylose or arabinose) or a sugar alcohol (such as sorbitol, xylitol or erythritol) attached to a reducing end of panose.

The pentasaccharide may include a homooligosaccharide such as maltopentaose or isomaltopentaose; and a heterooligosaccharide such as a pentaose having a disaccharide attached to a reducing end of panose. The pentaose having a disaccharide attached to a reducing end of panose is also disclosed in, for example, Japanese Patent Application Laid-Open No. 215892/1998 (JP-10-215892A), and may include a pertaose having a disaccharide (such as sucrose, lactose, cellobiose or trehalose) attached to a reducing end of panose.

Examples of the hexasaccharide may include a homooligosaccharide such as maltohexaose or isomaltohexaose.

The oligosaccharide preferably comprises at least a tetrasaccharide from the viewpoint of a melt-kneading property with the organic solid component.

The oligosaccharide may be an oligosaccharide composition produced by decomposition of a polysaccharide. The oligosaccharide composition usually contains a tetrasaccharide. The oligosaccharide composition may include, for example, a starch sugar (a saccharification product of a starch (or a saccharified starch)), a galactooligosaccharide, a coupling sugar, a fructooligosaccharide, a xylooligosaccharide, a soybean oligosaccharide, a chitin oligosaccharide, and a chitosan oligosaccharide.

For example, the starch sugar is an oligosaccharide composition obtained by making an acid or glucoamylase or the like act on a starch, and may be a mixture of an oligosaccharide obtained by bonding a plurality of glucoses to each other. The starch sugar may include, for example, a reduced starch-saccharified manufactured by Towa Chemical Industry Co., Ltd. (brand name "PO-10", the tetrasaccharide content is not less than 90% by weight).

The galactooligosaccharide is an oligosaccharide composition obtained by making β-galactosidase or the like act on lactose, and may be a mixture of galactosyllactose and a galactose-(glucose)$_n$ ("n" denotes an integer of 1 to 4).

The coupling sugar is an oligosaccharide composition obtained by making cyclodextrin synthetase (CGTase) act on a starch and sucrose, and may be a mixture of a (glucose)$_n$-sucrose ("n" denotes an integer of 1 to 4).

The fructooligosaccharide is an oligosaccharide composition obtained by making fructofuranosidase act on sucrose, and may be a mixture of a sucrose-(fructose)$_n$ ("n" denotes an integer of 1 to 4).

Concerning these oligosaccharide compositions, in order to inhibit rapid decrease of the viscosity in melt-kneading, the content of the trisaccharide or the tetrasaccharide (in particular, the tetrasaccharide) in the oligosaccharide composition may be, for example, not less than 60% by weight (about 60 to 100% by weight), preferably not less than 70% by weight (about 70 to 100% by weight), more preferably not less than 80% by weight (about 80 to 100% by weight), and particularly not less than 90% by weight (about 90 to 100% by weight).

The oligosaccharide may be a reducing-type (maltose-type), or a non-reducing type (trehalose-type). The reducing-type oligosaccharide is preferred because of excellence in heat resistance.

The reducing-type oligosaccharide is not particularly limited to a specific one as far as the oligosaccharide has a free aldehyde group or ketone group to exhibit a reducing property. For example, the reducing-type oligosaccharide may include a disaccharide such as kojibiose, nigerose, maltose, isomaltose, sophorose, laminaribiose, cellobiose, gentiobiose, lactose, palatinose, melibiose, rutinose, primeverose or ruranose; a trisaccharide such as maltotriose, isomaltotriose, panose, cellotriose, manninotriose or solatriose; a tetrasaccharide such as maltotetraose, isomaltotetraose, cellotetraose or lychnose; a pentasaccharide such as maltopentaose or isomaltopentaose; and a hexasaccharide such as maltohexaose or isomaltohexaose.

Since the oligosaccharide is generally a natural polysaccharide derivative, or a product derived from a natural product being manufactured by reducing the derivative, use of the oligosaccharide can reduce in the burden on the environment.

The flowability of the organic solid component and that of the auxiliary component may be the same, or different. In order to effectively disperse the organic solid component and the auxiliary component by kneading, it is desirable that the oligosaccharide has a high viscosity. More specifically, in the case where the viscosity of the 50% by weight aqueous solution of the oligosaccharide is measured at a temperature of 25° C. by using a B-type viscometer, the viscosity is not lower than 1 Pas (e.g., about 1 to 500 Pa·s), preferably not lower than 2 Pas (e.g., about 2 to 250 Pas, and in particular about 3 to 100 Pas), more preferably not lower than 4 Pas (e.g., about 4 to 50 Pas), and particularly not lower than 6 Pa·s (e.g., about 6 to 50 Pas), and it is preferred to use an oligosaccharide having a high viscosity.

Moreover, the melting point or softening point of the oligosaccharide (B1) is preferably higher than the heat distortion temperature of each organic solid material (e.g., a polymer) constituting the organic solid component (e.g., a polymer component) (A) (e.g., a melting point or softening point of the organic solid component (A), and a Vicat softening temperature defined by JIS K 7206). Incidentally, depending on the kind or species of the oligosaccharide [e.g., in the case of a starch sugar such as a reduced starch-saccharified], the oligosaccharide sometimes decomposed (thermally decomposed) without showing a melting point or softening point. In such a case, the decomposition temperature may be considered as the "melting point or softening point" of the oligosaccharide (B1).

The temperature difference between the melting point or softening point of the oligosaccharide (B1) and the heat distortion temperature of each organic solid material (e.g., a polymer) constituting the organic solid component (A) is, for example, not less than 1° C. (e.g., about 1 to 80° C.), preferably not less than 10° C. (e.g., about 10 to 70° C.), and more preferably not less than 15° C. (e.g., about 15 to 60° C.). The melting point or softening point of the oligosaccharide (B1) may be selected from the range of 70 to 300° C. depending on the kind of the organic solid component (A) and other factor(s), and may be, for example, about 90 to 290° C., preferably about 100 to 280° C. (e.g., about 110 to 270° C.), and more preferably about 120 to 260° C. (e.g., about 130 to 260° C.). Incidentally, an anhydride of an oligosaccharide generally has a high melting point or softening point. For example, in the case of a trehalose, the melting point of the dihydrate is 97° C. and that of the anhydride is 203° C. In the case where the melting point or softening point of the oligosaccharide is higher than the heat distortion temperature of each organic solid material (e.g., a polymer) constituting; the organic solid component (A), the oligosaccharide can be not only prevented from rapid deterioration of the viscosity in melt-kneading but also inhibited from thermal degradation.

(B2) Water-Soluble Plasticizing Component

The water-soluble plasticizing component (B2) is enough to just express a phenomenon that the oligosaccharide (B1) hydrates to turn into a syrup state, and may include, for example, a saccharide, and a sugar alcohol. These plasticizing components may be used singly or in combination.

(a) Saccharide

As the saccharide, a monosaccharide and/or a disaccharide is usually employed for plasticizing the oligosaccharide (B1) effectively. These saccharides may be used singly or in combination.

Examples of the monosaccharide may include a triose, a tetrose, a pentose, a hexose, a heptose, an octose, a nonose, and a decose. These compounds may be an aldose or ketose compound, a dialdose compound (for example, a compound which is a saccharide derivative and has aldehyde groups in both ends of the carbon chain, such as tetraacetylgalactohexodialdose, ido-hexodialdose or xylo-pento-dialdose), a monosaccharide having a plurality of carbonyl groups (e.g., an aldoalko-ketose such as osone or onose), a monosaccharide having a methyl group (e.g., a methyl sugar such as altromethylose), a monosaccharide having an acyl group (in particular, e.g., a $C_{2-4}$acyl group such as acetyl group) (for example, an acetylated product of the above-mentioned aldose compound, e.g., an acetylated product such as a pentaacetylated product of an aldehyde glucose), a saccharide having an introduced carboxyl group (e.g., a saccharic acid or a uronic acid), a thiosugar, an amino sugar, a deoxy sugar, or others.

Concrete examples of such a monosaccharide may include a tetrose (e.g., erythrose, and threorose), a pentose (e.g., arabinose, ribose, lyxose, deoxjribose, and xylose), and a hexose (e.g., allose, altrose, glucose, mannose, gulose, idose, galactose, fructose, sorbose, fucose, rhamnose, talose, galacturonic acid, glucuronic acid, mannuronic acid, and glucosamine).

Moreover, the monosaccharide may be a cyclic isomer having a cyclic structure formed through a hemiacetal linkage. It is not necessary that the monosaccharide has an optical activity (or rotatory polarization), and the monosaccharide may be any one of D-form, L-form, or DL-form. These monosaccharides may be used singly or in combination.

The disaccharide is not particularly limited to a specific one as far as the disaccharide can plasticize the oligosaccharide (B1). For example, among the above-mentioned disaccharides, there may be exemplified a disaccharide having a low melting point or low softening point (e.g., gentiobiose, melibiose, and trehalose (dihydrate)), and a disaccharide corresponding to a homo- and heterodisaccharide of the above-mentioned monosaccharide (e.g., an aldobiouronic acid such as glucuronoglucose in which glucuronic acid binds to glucose through an α-1,6-glycoside linkage).

The saccharide is preferably a reducing sugar in terms of having an excellent thermal stability. Examples of such a saccharide include a free monosaccharide, and in addition, a reducing sugar having a low melting point or low softening point (e.g., gentiobiose, and melibiose) among the disaccharides.

(b) Sugar Alcohol

As the sugar alcohol, a linear (or chain) sugar alcohol such as an alditol (glycitol) or a cyclic sugar alcohol such as an inositol may be used, and usually, the linear sugar alcohol may be employed. These sugar alcohols may be used singly or in combination.

Examples of the linear sugar alcohol may include a tetrytol (e.g., threitol, and erythritol), a pentitol [e.g., pentaerythritol, arabitol, ribitol (adonitol), xylitol, and lyxitol], a hexitol [e.g., sorbitol, mannitol, iditol, gulitol, talitol, dulcitol (galactitol), allo-dulcitol (allitol), and altritol], a heptitol, an octitol, a nonitol, a decitol, and a dodecitol.

Among these sugar alcohols, the preferred sugar alcohol includes erythritol, pentaerythritol, arabitol, ribitol, xylitol, sorbitol, dulcitol and mannitol. The sugar alcohol often comprises at least one sugar alcohol selected from the group consisting of erythritol, pentaerythritol and xylitol.

The plasticizing component (B2) may be a liquid (or in a syrup state) at a room temperature (e.g., about 15 to 20° C.), and from the viewpoint of handleability and others, the plasticizing component (B2) is usually a solid in many cases. In the case where the auxiliary component (B) comprises the oligosaccharide (B1) and the plasticizing component (B2), the plasticizing component (B2) can effectively plasticize or soften the oligosaccharide (B1) even when the oligosaccharide (B1) is a thermally decomposable oligosaccharide not having a clear melting point or softening point.

The melting point or softening point of the plasticizing component (B2) is usually not higher than the heat distortion temperature of at least one organic solid material (or each organic solid material) among a plurality of organic solid materials (e.g., polymers) constituting the organic solid component (A) (for example, not higher than a melting point or softening point of the organic solid component (A), and a Vicat softening temperature defined by JIS K 7206). Incidentally, some plasticizing components are molten at a temperature lower than the actual melting point when coexisting with the oligosaccharide while having a high melting point (e.g., a melting point of not lower than 200° C.). For example, pentaerythritol exerts a plasticizing effect on the oligosaccharide and melts at a temperature (e.g., at about 160 to 180° C.) lower than the actual melting point (260° C.). The plasticizing component having such a high melting point cannot be singly utilized because of being not molten at the heat distortion temperature of the organic solid component (e.g., a polymer component). However, such a plasticizing component can be utilized effectively in combination with the oligosaccharide. Incidentally, in the plasticizing component exerting a plasticizing effect on the oligosaccharide (e.g., pentaerythritol) at a temperature lower than the actual melting point, the temperature at which a plasticizing effect on the oligosaccharide is exerted may be regarded as the "melting point or softening point" of the plasticizing component (B2).

The melting point or softening point of the auxiliary component (B) may be not higher or lower than the heat distortion temperature of each organic solid material (e.g., a polymer) constituting the organic solid component (A). It is sufficient that each organic solid material (e.g., a polymer) constituting the organic solid component (A) and the auxiliary component (B) are molten or soften at least at a kneading temperature (or fabrication temperature). For example, the temperature difference between the melting point or softening point of the auxiliary component (B) and the heat distortion temperature of each organic solid material (e.g., a polymer) constituting the organic solid component (A) may be selected from the range of 0 to 100° C. For example, the temperature difference may be about 3 to 80° C. (e.g., about 3 to 55° C.), preferably about 5 to 60° C. (e.g., about 5 to 45° C.), and more preferably about 5 to 40° C. (e.g., about 10 to 35° C.). Incidentally, in the case where the temperature difference between the melting point or softening point of the auxiliary component (B) and the heat distortion temperature of each organic solid material (e.g., a polymer) constituting the organic solid component (A) is small (e.g., in the case where the temperature difference is about 0 to 20° C.), there is an advantage that the dispersion shape can be fixed in a short time by an auxiliary component (B) (e.g., a sugar component) having a high solidification rate.

Further, the melt flow rate of the auxiliary component (B) (e.g., an auxiliary component comprising the oligosaccharide (B1) and the plasticizing component (B2)) may be, for example, not less than 1 (e.g., about 1 to 40), preferably not less than 5 (e.g., about 5 to 30), and more preferably not less than 10 (e.g., about 10 to 20) when measured the melt flow rate defined by JIS K 7210 at a temperature 30° C. higher than the heat distortion temperature of each organic solid material (e.g., a polymer) constituting the organic solid component (A) [e.g., at a temperature 30° C. higher than the lowest temperature of a melting point or softening point of the organic solid component (A) and the Vicat softening temperature (the melting point or softening point, the Vicat softening temperature)].

In the auxiliary component (B), the ratio (weight ratio) of the plasticizing component (B2) is selected from the range that the plasticizing component can plasticize the oligosaccharide (B1) efficiently without localizing by aggregation or other reason accompanying melt-kneading. For example, the ratio of the oligosaccharide (B1) relative to the plasticizing component (B2) [the oligosaccharide (B1)/the plasticizing component (B2)] may be selected from 99/1 to 50/50, and may be preferably about 95/5 to 60/40 and more preferably about 90/10 to 70/30.

The ratio (weight ratio) of the organic solid component (A) relative to the auxiliary component (B) may be selected depending on the kinds or viscosities of the organic solid component and the auxiliary component, the miscibility between the organic solid component and the auxiliary component, or other factor(s), and is not particularly limited to a specific one. The ratio [the organic solid component (A)/the auxiliary component (B)] may be usually selected from the range that formability (or moldability) of the dispersion composition is not impaired, and may be, for example, about 55/45 to 1/99, preferably about 50/50 to 5/95 and more preferably about 45/55 to 10/90.

In the present invention, the dispersion composition or the composition may contain, if necessary, various additives, for example, other additive such as a filler (e.g., a particulate filler, and a fibrous filler such as a glass fiber), a plasticizer or a softener, an agent for imparting photodegradable property (e.g., an anatase-type titanium oxide), a lubricant, a stabilizer (e.g., a heat stabilizer, an antioxidant, an ultraviolet ray absorbing agent, and a weather (light) stabilizer), an ultraviolet-scattering agent (e.g., a powder of a metal oxide such as titanium oxide, zirconium oxide, zinc oxide, or iron oxide), a dispersing agent, a flame retardant, an antistatic agent, a coloring agent [for example, a dye such as an oil-soluble organic dye; an inorganic or organic pigment (e.g., including a ferromagnetic material such as a ferromagnetic metal (powder) such as iron, cobalt, or nickel; a ferromagnetic alloy (powder) such as a magnetite or a ferrite; or a ferromagnetic metal oxide (powder) such as magnetic iron oxide)], a charge control agent (e.g., a positive charge control agent such as a nigrosin dye, a triphenylmethane-series dye, a quaternary ammonium salt, a guanidine compound, an imidazole compound, or an amine-series compound; and a negative charge control agent such as a metal complex of salicylic acid, a metal complex of an azo dye, a copper phthalocyanine dye, a nitroimidazole derivative, or a urea derivative), a superplasticizer (or an agent for imparting fluidization), a wax [for example, an olefinic wax such as a polyethylene wax, an ethylene copolymer wax, or a polypropylene wax; a paraffin wax; a higher fatty acid or a derivative thereof (e.g., a salt, a polyhydric alcohol ester, and an amide); and an ester-series wax], or a crosslinking agent. Incidentally, the additive may be contained in any of the dispersed phase (e.g., each organic solid material constituting the organic solid component (A)) and the matrix constituting the dispersion composition.

The additive may be selected depending on applications of the multiple particle (e.g., a multiple polymer particle) or others. For example, in an application of a cosmetic (e.g., a foundation, a face powder, and a blusher), the ultraviolet ray absorbing agent (e.g., a benzophenone-series absorbing agent, a cinnamic acid-series absorbing agent, a p-aminobenzoic acid-series absorbing agent, a salicylic acid-series absorbing agent, a dibenzoylmethane-series absorbing agent, urocanic acid or an ester thereof, β-isopropyl-furanone, and β-carotene), the ultraviolet-scattering agent, the coloring agent, and others may be used. In an application of image recording material such as a toner, for example, the charge control agent, the superplasticizer, the wax, the coloring agent, and others may be used. Moreover, in an application of paint and varnish, or the like, for example, there may be used the crosslinking agent, the weather (light) stabilizer, the ultraviolet ray absorbing agent, the superplasticizer, and the coloring agent.

In these additives, the amount of each additive may be an effective amount, and for example, the total amount of the additives may be selected from the range of about 0 to 100 parts by weight relative to 100 parts by weight of the organic solid component. For example, the total amount of the additives may be about 0 to 50 parts by weight (e.g., about 0 to 30 parts by weight), preferably about 0.05 to 20 parts by weight (e.g., about 0.1 to 20 parts by weight), and more preferably about 0.1 to 10 parts by weight (e.g., about 0.5 to 10 parts by weight), relative to 100 parts by weight of the organic solid component.

In the dispersion composition of the present invention, the average particle size of the dispersed phase is not particularly limited to a specific one, and may be selected from the range of about 0.1 μm to 1 mm (e.g., about 0.1 to 800 μm) as usage. For example, the average particle size may be, for example, about 0.1 to 500 μm, preferably about 0.1 to 100 μm (e.g., about 0.5 to 80 μm), more preferably about 0.2 to 50 μm (e.g., about 0.5 to 50 μm), and particularly about 1 to 40 μm (e.g., about 1 to 20 μm). Moreover, the average particle size of the dispersed phase may be, for example, about 0.1 to 10 μm (e.g., about 0.2 to 5 μm), and preferably about 0.5 to 3 μm (e.g., about 0.5 to 2 μm).

In the present invention, the particle size of the dispersed phase can be uniformized and the particle size distribution of the particle size can be narrowed. The coefficient (%) of variation of the average particle size in the dispersed phase ([the standard deviation of the particle size/the average particle size]×100) may be, for example, not more than 60 (e.g., about 5 to 60), and more preferably not more than 50 (e.g., about 10 to 50).

In the dispersion composition of the present invention, it is sufficient that the configuration (or shape) of the dispersed phase is a particle shape. For example, the configuration (or shape) of the dispersed phase may be a spherical shape, an elliptical shape, a polyhedral shape, a prismatic shape, a columnar (or cylindrical) shape, a rod-like shape, and an amorphous shape, and others. The preferred shape of the disperse phase is a spherical shape (e.g., a finely spherical shape). The spherical dispersion composition (or spherical particle) is not limited to a finely spherical shape, and for example, includes a shape having a length ratio of a major axis relative to a minor axis of, e.g., about 1.5/1 to 1/1. The length ratio of the major axis relative to the minor axis [the major axis/the minor axis] may be preferably about 1.3/1 to 1/1 (e.g., about 1.2/1 to 1/1), and more preferably about 1.1/1 to 1/1.

In the case where the dispersed phase has a core-shell structure, the thickness of the shell may be appropriately controlled as usage by suitably adjusting the proportion of the organic solid material constituting the shell relative to the organic solid material constituting the core, the combination of these organic solid materials, the affinity relative to the auxiliary component, and others. The thickness of the shell may be selected from the wide range of not more than 5 μm, for example, from about 10 nm to 5 μm. The thickness of the shell may be preferably not more than 1 μm (e.g., about 10 ran to 1 μm), and more preferably about 20 to 800 nm (e.g., about 30 to 500 nm).

The dispersion composition may be prepared by kneading a plurality of organic solid materials constituting the organic solid component (A) with the auxiliary component (B), and usually, the kneaded composition is often shaped (or molded) to prepare a preliminary shaped article. The kneading operation may be carried out by using a conventional kneading machine (e.g., a uniaxial or biaxial screw extruder, a kneader, and a calender roll). Moreover, in advance of kneading, each of components may be preliminarily converted into a powder form by a machine such as a freeze grinder or may be preliminarily kneaded by a Henschel mixer, a tumbler mixer, a ball mill or others.

Examples of the shaping (or molding) method may include an extrusion molding, an injection molding, a blow molding, and a calender molding. In view of productivity or easiness of processing, an extrusion molding or an injection molding is usually applied. The shape of the preliminary shaped article (or dispersion composition) is not particularly limited to a specific one, and may be a zero-dimensional shape (e.g., a particle shape, and a pellet shape), a one-dimensional shape (e.g., a strand shape, and a rod or bar shape), a two-dimensional shape (e.g., a plate shape, a sheet shape, and a film shape), a three-dimensional shape (e.g., a tubular shape, and a block shape), and others. Considering the elution property (or elution capability) of the auxiliary component, it is desirable to process (or shape) the dispersion composition into a strand shape, a rod or bar shape, a sheet shape, or a film shape.

The water-soluble auxiliary component may be eluted from the kneaded matter, and the water-soluble auxiliary component is usually eluted by shaping (or molding) after kneading.

Incidentally, it is possible to appropriately set the kneading temperature or processing (or shaping) temperature (or fabrication temperature) depending on a raw material to be used (e.g., the organic solid component and the auxiliary component). For example, the kneading temperature or processing temperature is about 90 to 300° C., preferably about 110 to 260° C. (e.g., about 170 to 250° C.), more preferably about 140 to 240° C. (e.g., about 170 to 240° C.), and particularly about 170 to 230° C. (e.g., about 180 to 220° C.). In order to avoid thermal decomposition of the auxiliary component (the oligosaccharide and the plasticizing component), the kneading temperature or processing temperature may be set to a temperature not higher than 230° C. Moreover, the kneading time may be, for example, selected from the range of 10 seconds to one hour, and is usually about 30 seconds to 45 minutes, and preferably about 1 to 30 minutes (e.g., 1 to 10 minutes).

The molten mixture (e.g., a kneaded matter, and a preliminary shaped article) obtained by kneading and/or processing (or fabrication) may be suitably cooled, if necessary. By cooling the molten mixture in such a way, even in the case where the organic solid component (A) (e.g., at least one member out of a plurality of organic solid materials) and the auxiliary component (B) are miscible with each other in the molten state, a dispersed phase can be formed due to differences in surface tension and solidification rate such as crystallization rate between the organic solid component and the auxiliary component along with cooling.

The cooling temperature may be at least about 10° C. lower than the heat distortion temperature of each organic solid material (e.g., a polymer) constituting the organic solid component (A) or the melting point or softening point of the auxiliary component (B), and for example, may be about 10 to 100° C. lower than the above temperature (the heat distortion temperature of the organic solid material (e.g., a polymer), or the melting point or softening point of the auxiliary component), preferably about 15 to 80° C. lower than the above temperature, and more preferably about 20 to 60° C. lower than the above temperature. Specifically, for example, the cooling temperature may be selected from the range of 5 to 150° C. depending on the kind of the organic solid material or the auxiliary component, and may be, for example, about 10 to 120° C. (e.g., about 10 to 60° C.), preferably about 15 to 100° C. (e.g., about 15 to 50° C.), and more preferably about 20 to 80° C. (e.g., about 20 to 40° C.). The cooling time may be suitably set according to the kind of the organic solid component or the auxiliary component, the cooling temperature, and others, and may be selected, for example, from the broad range of 30 seconds to 20 hours. For example, the cooling time may be about 45 seconds to 10 hours, preferably about one minute to 5 hours (e.g., about one minute to one hour), and more preferably about 1.5 to 30 minutes.

Moreover, by adjusting the miscibility between the organic solid component and the auxiliary component, the kneading conditions (e.g., the kneading time, and the kneading temperature), the processing temperature and the cooling conditions (e.g., the cooling time, and the cooling temperature), the average particle size of the dispersed phase (or particle) may be changed or the width of the particle size distribution may be further narrowed.

Thus obtained dispersion composition has a phase separation structure in which the auxiliary component (B) forms a continuous phase of en islands-in-the-sea structure and the organic solid component (A) forms an independent dispersed phase thereof. Therefore, the auxiliary component can be quickly eluted or extracted to give the dispersed phase (the phase of the organic solid component) as a multiple particle (e.g., a multiple polymer particle).

[Production Process of Multiple Particle]

According to the present invention, a multiple particle (e.g., a multiple polymer particle) which comprises the organic solid component (A) corresponding to the dispersed phase and containing a plurality of organic solid materials (e.g., polymers) is produced by eluting the water-soluble auxiliary component (B) constituting a matrix from the dispersion composition.

The elution (or washing) of the water-soluble auxiliary component (B) may be carried out by using an aqueous solvent, for example, water, and a water-soluble solvent [e.g., an alcohol compound (e.g., methanol, ethanol, propanol, isopropanol, and butanol), and an ether compound (e.g., a cellosolve, and a butyl cellosolve)]. These aqueous solvents may be used singly or in combination.

The preferred elution solvent is water because of the low burden on the environment and the industrial cost reduction.

The elution of the auxiliary component (B) may be conducted by a conventional method, for example, by immersing and dispersing the dispersion composition (or preliminary shaped article) in the aqueous medium, and eluting or washing the auxiliary component from the dispersion composition (or moving over the auxiliary component to the phase of the aqueous solvent). In the case where the dispersion composition (or preliminary shaped article thereof) is immersed in the aqueous medium, the water-soluble auxiliary component forming the matrix of the dispersion composition is gradually eluted and the dispersed phase (particle) is dispersed in the mixture obtained by the elution. In order to accelerate the dispersion and elution of the auxiliary component, stirring or other means may be suitably conducted.

The auxiliary component may be eluted, for example, under an applied pressure, and usually, can be eluted under an atmospheric pressure (e.g., about $1 \times 10^5$ Pa) or a reduced pressure. Moreover, the elution temperature of the auxiliary component may be appropriately established depending on the organic solid component and the auxiliary component. The elution temperature of the auxiliary component is usually a temperature lower than the melting point or softening point of the organic solid material, and is, for example, about 10 to 100° C., preferably about 25 to 90° C., and more preferably 30 to 80° C. (e.g., about 40 to 80° C.). Since the water-soluble auxiliary component of the present invention is easily soluble in water, a large amount of water is not required. Moreover, since the viscosity of the resultant mixture is low, the obtained particle can be easily collected.

The multiple particle may be collected from a dispersion liquid containing the dispersed particle by a conventional separation (collecting) method, e.g., filtration and centrifugation. It is desirable that the obtained shaped article has substantially no residual auxiliary component. However, for example, in view of cost reduction of the washing process, the multiple particle may have a small amount of the residual auxiliary component. The small amount of the auxiliary component in the multiple particle does not significantly affect the obtained particle and has a high safety because the auxiliary component is a compound derived from a natural product (including a food product or a food additive). Incidentally, the proportion of the auxiliary component (B) in the particle may be, for example, not mere than 3% by weight.

Incidentally, the auxiliary component eluted or extracted with the solvent may be collected by a conventional separation means (e.g., distillation, concentration, recrystallization, and drying (freeze drying)).

The multiple particle (e.g., a multiple polymer particle) of the present invention corresponds to the dispersed phase of the dispersion composition, and the configuration (or shape), the average particle size and the coefficient of variation of the average particle size of the particle may be selected from the same range as the above-mentioned dispersed phase. Moreover, the length ratio of the major axis relative to the minor axis in the particle may be also selected from the same range as the above-mentioned dispersed phase. Incidentally, the configuration (or shape) or size of the particle is retained that of the intact dispersed phase unless the organic solid component (A) is eluted in the elution solvent (aqueous solvent). Incidentally, if necessary, the particle size of the multiple particle may be made uniform by a means such as classification.

INDUSTRIAL APPLICABILITY

Since the multiple particle (e.g., a multiple polymer particle) of the present invention comprises a plurality of organic solid materials (e.g., polymers), various functions unobtainable from a particle comprising a single component (e.g., a single polymer component) can be imparted to the multiple particle, depending on properties of the organic solid materials (e.g., polymers). For example, in the case of using a plurality of organic solid materials (e.g., polymers) different in refraction index difference from each other, a high light scattering effect is obtained, and therefore, the multiple particle may be utilize in an application of a cosmetic (e.g., a foundation, a face powder, a blusher, and an eye shadow). Moreover, the multiple particle having a core-shell structure may be applied for a variety of applications by utilizing a difference between a surface property and an internal property thereof. Further, the multiple particle may be also utilized for an image-recording material such as an ink (including a polymer ink) or a colored toner used for an ink jet printing or others, and a paint and varnish or a coating agent (e.g., a powdered paint, or a coating material for slurry painting). Incidentally, the multiple particle may be used for improving the mix aptitude to other fine particle (e.g., an inorganic fine particle), or may be used as an antiblocking agent (e.g., an antiblocking agent for a shaped article), a spacer (e.g., a spacer for a liquid crystal), an additive for sheet or film, an abrasive for chemical and mechanical polishing (CMP) of semiconductor, and others.

Moreover, the multiple polymer particle obtained by using a biodegradable polymer component is useful for a raw material or additive in a fine chemical field such as an agricultural chemical, a medicine (or a pharmaceutical), a paint and varnish (e.g., a powdered paint, and a ship bottom paint), a coating agent or an adhesive agent because of being excellent in biodegradability. Further, the multiple polymer particle may be also utilized as an additive to a film or sheet for agriculture, forestry and fisheries, civil engineering, and construction; a material for sanitary goods (e.g., a disposable diaper); a medical material requiring biodegradation and bioabsorbability; or a sustained release material requiring sustained release.

EXAMPLES

The following examples are intended to describe this invention in further detail and should by no means be interpreted as defining the scope of the invention.

Examples 1 to 6

In each Examples, a polymer composition comprising a thermoplastic resin component and a water-soluble auxiliary component in the formulation shown in Table 1 was melt-kneaded at a preset temperature of 200° C. for 5 minutes by using a brabender (manufactured by Toyo Seiki Seisaku-sho, Ltd., laboplastmill), and then cooled to prepare a dispersion composition. The obtained dispersion composition was immersed in hot water of 60° C. to give a suspension of the polymer particle. The insoluble matter was separated from the suspension with a membrane (pore size: 0.45 μm) made of a polyvinylidene fluoride to collect the fine particle of the polymer.

Figure 1:
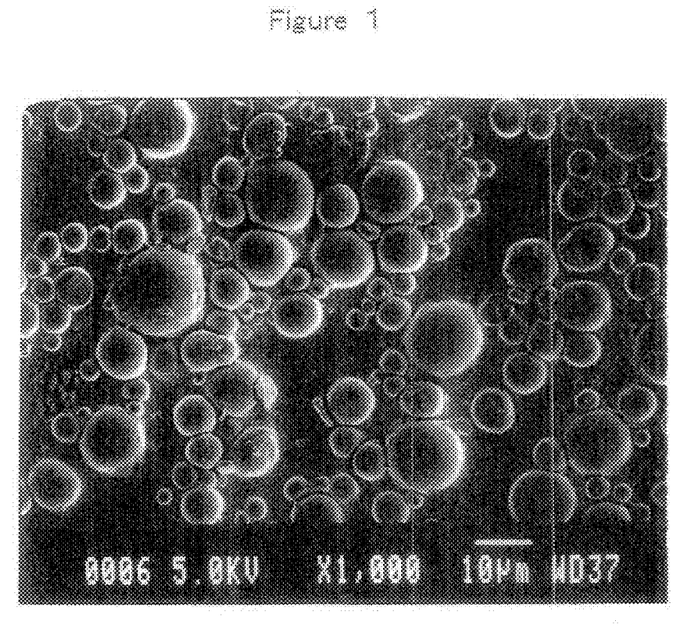
FIG. 1 is a transmission electron micrograph of a multiple polymer particle obtained in Example 2.
Figure 2:
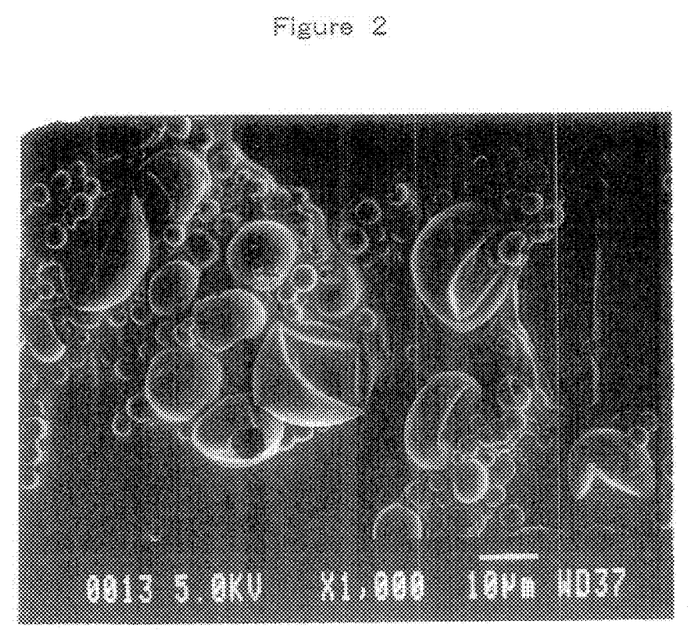
FIG. 2 is a transmission electron micrograph showing a particle state after treating the multiple polymer particle of Example 2 with tetrahydrofuran.

For reference, FIG. 1 shows a transmission electron micrograph (1000 magnifications) of a multiple polymer particle obtained in Example 2. Moreover, FIG. 2 shows a transmission electron micrograph (1000 magnifications) representing a particle state after treating the multiple polymer particle obtained in Example 2 with tetrahydrofuran.

Incidentally, components used in Examples and evaluation methods of the obtained fine particle are described below. The results are shown in Table 1.

(Polymer Component)

Polymer 1: Polystyrene polymer (manufactured by Toyo Styrene Co., Ltd., "GPPS HRM63C")

Polymer 2: Styrene-butadiene-styrene block copolymer (SBS polymer) (manufactured by JSR Corporation, "TR2003")

Polymer 3: Polyamide 12 polymer (manufactured by Daicel-Degussa Ltd., "DIAMID L1640")

Polymer 4: Polybutylene succinate-polycaprolactone copolymer (manufactured by Daicel Chemical Industries, Ltd., "CELLGREEN CBS17X")

Polymer 5: Polylactic acid (manufactured by Mitsui Chemicals, Inc., "LACEA H-100PL")

(Water-Soluble Auxiliary Component)

(B1) Oligosaccharide: Starch sugar (manufactured by Towa Chemical Industry Co., Ltd., reduced saccharification product of a starch "PO-10", a viscosity of a 50% by weight aqueous solution measured at 25° C. by a B-type viscometer: 6.5 Pa·s)

(B2) Plasticizing component: Sugar alcohol (manufactured by Towa Chemical Industry Co., Ltd., "Marinecrystal D(−)mannitol")

(Structural Observation of Multiple Polymer Particle)

Figure 3:
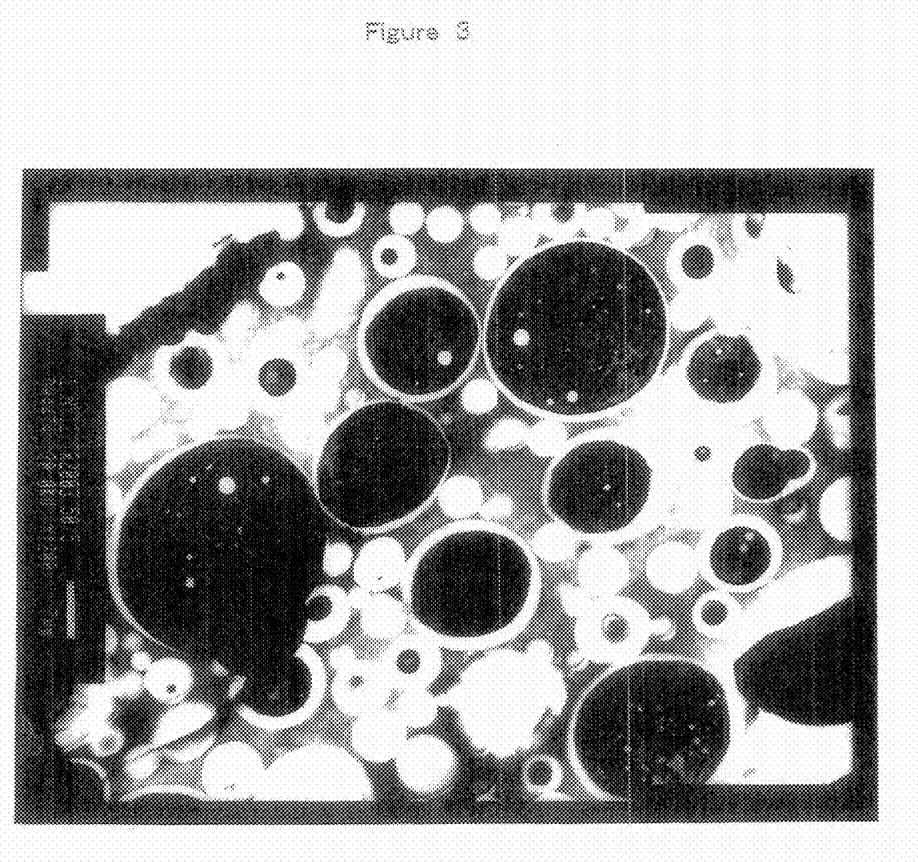
FIG. 3 is a transmission electron micrograph of a cross section of the multiple polymer particle obtained in Example 2.

A Polymer fine particle was mixed with a chemically reactive adhesive of epoxy polymer-series (manufactured by Konishi Co., Ltd., "BONDQUICK 5") to make a massive product containing the polymer particle dispersed therein, and the massive product was cut to a thickness of about 0.05 μm to 0.2 μm by a microtome to give an ultrathin section. Thereafter, the polymer particle in the ultrathin section was stained with a coloring matter capable of staining the Polymer component (A) and the Polymer component (B) distinctively (e.g., osmic acid, and ruthenic acid), and was observed about the structure by using a transmission electron microscope. For reference, FIG. 3 shows a transmission electron micrograph of the state (the cross section of the particle) after staining the multiple polymer particle obtained in Example 2.

(Average Particle Size of Polymer Particle)

The collected resinous fine particle was dried, and then the configuration (or shape) of the fine particle was observed by using a scanning electron microscope. Moreover, the appropriate amount of the dry Polymer fine particle was dispersed in pure water again to prepare a suspension. Then, the number average particle size of the resinous fine particle was determined by using a laser diffraction particle size analyzer (manufactured by Shimadzu Corporation, "SALD-2000J"). Further, concerning the resinous fine particle, the standard deviation and the coefficient of variation relative to 100 particles selected at random were calculated.

TABLE 1

|  | Polymer (A1) [parts] | Polymer (A2) [parts] | (B1) [parts] | (B2) [parts] | Number average particle size [μm] | Particle shape | Particle structure | Shell thickness [μm] |
|---|---|---|---|---|---|---|---|---|
| Ex. 1 | Polymer 1 20 | Polymer 3 20 | 75 | 25 | 7.2 | Finely spherical shape | Core-shell | <1 |
| Ex. 2 | Polymer 2 20 | Polymer 3 20 | 75 | 25 | 14 | Finely spherical shape | Core-shell | <1 |
| Ex. 3 | Polymer 2 30 | Polymer 3 10 | 75 | 25 | 11 | Finely spherical shape | Core-shell | <1 |
| Ex. 4 | Polymer 2 20 | Polymer 4 20 | 75 | 25 | 5.8 | Finely spherical shape | Core-shell | <1 |
| Ex. 5 | Polymer 1 20 | Polymer 5 20 | 75 | 25 | 6.4 | Finely spherical shape | Core-shell | <1 |
| Ex. 6 | Polymer 4 20 | Polymer 5 20 | 75 | 25 | 6.3 | Finely spherical shape | Core-shell | <1 |

(In Table, "parts" means "parts by weight")

In each of Examples 1 to 6, core-shell finely spherical multiple polymer particles comprising the thermoplastic resin (A) as the shell were obtained. The shell thickness of each obtained particle was not more than 1 μm. Moreover, from FIG. 3, in a core-shell finely spherical multiple polymer particle containing the polyamide 12 polymer as the shell and the styrene-butadiene-styrene block copolymer as the nucleus (core), it was confirmed that the butadiene part of the styrene-butadiene block copolymer forming the core was stained with osmic acid and observed black by a transmission electron microscope and that the polyamide 12 polymer formed the shell. This is clear in view of the fact that treatment of the polymer particle shown in FIG. 1 with tetrahydrofuran, which dissolves a styrene-butadiene-styrene block copolymer, induces exudation of the styrene-butadiene-styrene copolymer due to collapse of the shell comprising the polyamide polymer and makes the shell a broken state, as shown in FIG. 2.

The invention claimed is:

1. A process for producing a particle having a core-shell structure and comprising an organic solid component (A) containing a thermoplastic polymer (A1) and a thermoplastic hydrophilic polymer (A2), which comprises
kneading the organic solid component (A) with a water-soluble auxiliary component (B) containing at least an oligosaccharide (B1) to provide a composition which has a disperse system and comprises a matrix comprising the water-soluble auxiliary component (B) and a particulate dispersed phase comprising the organic solid component (A) and dispersed in the matrix, wherein the particulate dispersed phase corresponds to the particle having a core-shell structure, and
eluting the auxiliary component (B) from the composition; and
wherein the core of the particle contains the polymer (A1) and the shell of the particle contains the hydrophilic polymer (A2) which has a hydrophilicity higher than the polymer (A1),
wherein the particle is spherical and has an average particle size of 0.1 to 100 μm, a coefficient of variation of the average particle size of not more than 60.

2. The process according to claim 1, which comprises eluting the auxiliary component (B) from the composition by an aqueous solvent.

3. The process according to claim 1, which comprises eluting the auxiliary component (B) from the composition by water.

4. The process according to claim 1, which comprises kneading the organic solid component (A) with the water-soluble auxiliary component (B), in a molten state, to provide the composition having a disperse system, solidifying the composition, and eluting the auxiliary component (B) from the solidified composition.

5. The process according to claim 1, wherein the thermoplastic polymer (A1) and the thermoplastic hydrophilic polymer (A2) are immiscible with each other and different in affinity relative to the auxiliary component (B) from each other.

6. The process according to claim 1, which produces a spherical particle having a length ratio of a major axis relative to a minor axis of 1.5/1 to 1/1.

7. The process according to claim 1, wherein the oligosaccharide (B1) comprises at least a tetrasaccharide.

8. The process according to claim 1, wherein the oligosaccharide (B1) comprises at least one member selected from the group consisting of a starch sugar, a galactooligosaccharide, a coupling sugar, a fructooligosaccharide, a xylooligosaccharide, a soybean oligosaccharide, a chitin oligosaccharide and a chitosan oligosaccharide.

9. The process according to claim 1, wherein the oligosaccharide (B1) has a viscosity of not lower than 1 Pa·s when a 50% by weight aqueous solution of the oligosaccharide is measured at a temperature of 25° C. by a B-type viscometer.

10. The process according to claim 1, wherein the auxiliary component (B) comprises the oligosaccharide (B1) and a water-soluble plasticizing component (B2) for plasticizing the oligosaccharide (B1).

11. The process according to claim 10, wherein the oligosaccharide (B1) shows a melting point or softening point or is decomposed at a temperature higher than each of heat distortion temperatures of the thermoplastic polymers (A1) and (A2), and the melting point or softening point of the plasticizing component (B2) is not higher than the heat distortion temperature of at least one of the thermoplastic polymers (A1) and (A2).

12. The process according to claim 10, wherein the plasticizing component (B2) comprises at least one member selected from the group consisting of a saccharide and a sugar alcohol.

13. The process according to claim 12, wherein the sugar alcohol comprises at least one member selected from the group of erythritol, pentaerythritol, arabitol, ribitol, xylitol, sorbitol, dulcitol and mannitol.

14. The process according to claim 10, wherein the ratio (weight ratio) of the oligosaccharide (B1) relative to the plasticizing component (B2) is 99/1 to 50/50.

15. The process according to claim 1, wherein
each of the thermoplastic polymers (A1) and (A2) has a Vicat softening temperature defined by JIS K 7206 of 60 to 300° C.;
the oligosaccharide (B1) has a viscosity of 3 to 100 Pa·s when the viscosity is measured using a 50% by weight aqueous solution of the oligosaccharide at a temperature of 25° C. by a B-type viscometer; and
the auxiliary component (B) has a melt flow rate defined by JIS K 7210 of not less than 1 when measured at a temperature 30° C. higher than the minimum point of the Vicat softening temperatures of the thermoplastic polymers (A1) and (A2).

16. The process according to claim 1, wherein the ratio (weight ratio) of the organic solid component (A) relative to the auxiliary component (B) is 55/45 to 1/99.

* * * * *